US011814392B2

(12) United States Patent
Mayor et al.

(10) Patent No.: US 11,814,392 B2
(45) Date of Patent: Nov. 14, 2023

(54) CHROMENOPYRIDINE-BASED COMPOUNDS AND METHODS OF MAKING AND USE THEREOF

(71) Applicant: Rosalind Franklin University of Medicine and Science, North Chicago, IL (US)

(72) Inventors: June A Mayor, North Chicago, IL (US); Shivaputra A. Patil, North Chicago, IL (US); Ronald S. Kaplan, North Chicago, IL (US)

(73) Assignee: Rosalind Franklin University of Medicine and Science, North Chicago, IL (US)

( * ) Notice: Subject to any disclaimer, the term of this patent is extended or adjusted under 35 U.S.C. 154(b) by 35 days.

(21) Appl. No.: 17/514,378

(22) Filed: Oct. 29, 2021

(65) Prior Publication Data

US 2022/0135581 A1    May 5, 2022

Related U.S. Application Data

(60) Provisional application No. 63/252,359, filed on Oct. 5, 2021, provisional application No. 63/107,299, filed on Oct. 29, 2020.

(51) Int. Cl.
*C07D 491/052*      (2006.01)
*A61P 35/00*        (2006.01)

(52) U.S. Cl.
CPC .......... *C07D 491/052* (2013.01); *A61P 35/00* (2018.01)

(58) Field of Classification Search
CPC .................. C07D 491/052; A61K 31/436
USPC .......................................... 546/101; 514/291
See application file for complete search history.

(56) References Cited

PUBLICATIONS

Bamerjee, et al., Molecules (2015), 20(9), 17152-17165. (Year: 2015).*
Patil, et al., Bioorganic & Medicinal Chemistry Letters (2017), 27(5), 1129-1135. (Year: 2017).*
Patil, et al., Bioorganic and Medicinal Chemistry Letters (2017), 27(5), 1129-1135. (Year: 2017).*
DeBerardinis, R.J., et al., "Fundamentals of Cancer Metabolism", Sci Adv., May 27, 2016, vol. 2(5), e1600200, pp. 1-18.
Hua, H., et al., "Targeting mTOR for Cancer Therapy", J. Hematol. Oncol., Jul. 5, 2019, vol. 12(1), 71, pp. 1-19.
Kopel, J., et al., "The Hepatic Plasma Membrane Citrate Transporter NaCT (SLC13A5) as a Molecular Target for Metformin", Sci. Rep., May 22, 2020, vol. 10(1), 8536, pp. 1-12.
Koundouros, N., and Poulogiannis, G., "Reprogramming of Fatty Acid Metabolism in Cancer", Br. J. Cancer, Jan. 2020, vol. 122(1), pp. 4-22.
Li, Z., et al., "Silencing of Solute Carrier Family 13 Member 5 Disrupts Energy Homeostasis and Inhibits Proliferation of Human Hepatocarcinoma Cells", J. Biol. Chem., Aug. 18, 2017, vol. 292(33), pp. 13890-13901.
McOmie, J.F.W., "Protective Groups in Organic Chemistry," Plenum Press, London and New York, 1973 (Abstract only).
Nie, R., et al., "Structure and Function of the Divalent anion/Na+ Symporter from Vibrio Cholerae and a Humanized Variant", Nat. Commun., Apr. 24, 2017, vol. 8, 15009, pp. 1-10.
Paredes, F., et al., "Metabolic Adaptation in Hypoxia and Cancer," Cancer Lett., Apr. 1, 2021, vol. 502, pp. 133-142.
Pavlova, N.N., and Thompson, C.B., "The Emerging Hallmarks of Cancer Metabolism", Cell Metab., Jan. 12, 2016, vol. 23(1), pp. 27-47.
Poolsri, W.A., et al., "Combination of Mitochondrial and Plasma Membrane Citrate Transporter Inhibitors Inhibits De Novo Lipogenesis Pathway and Triggers Apoptosis in Hepatocellular Carcinoma Cells", Biomed. Res. Int., Jan. 9, 2018, vol. 2018, 3683026, pp. 1-16.
Smith, M.B. and March, J., "March's Advanced Organic Chemistry: Reactions, Mechanisms and Structure", Fifth Edition, Wiley-Interscience, 2001 (Abstract only).
Snyder, L.R., and Kirkland, J.J., (editors), "Introduction to Modern Liquid Chromatography", 2nd Edition, John Wiley and Sons, 1979 (Abstract only).
Stahl, E., (editor), "The Historical Development of the Method", Thin Layer Chromatography, Springer-Verlag, New York, 1969, pp. 1-2.
Sun, J., et al., "Mitochondrial and Plasma Membrane Citrate Transporters: Discovery of Selective Inhibitors and Application to Structure/Function Analysis", Mol. Cell. Pharmacol., 2010, vol. 2(3), pp. 101-110.
Yang, J., et al., "Targeting PI3K in Cancer: Mechanisms and Advances in Clinical Trials", Mol. Cancer, Feb. 19, 2019, vol. 18(1), 26, pp. 1-28.
Greene, T.W., and Wuts, P.G.M., Protective Groups in Organic Synthesis, Third Edition, Wiley, New York, 1999, (Abstract only).
Gross, E., and Meienhofer, J., (editors), The Peptides: Protection of Functional Groups in Peptide Synthesis, vol. 3, Academic Press, London and New York, 1981, (Abstract only).
Vogel, A.I., A Textbook of Practical Organic Chemistry, Including Qualitative Organic Analysis, Fourth Edition, New York: Longman, 1978, (Abstract only).
Methoden der organischen Chemie, Houben-Weyl, 4th Sup. Edition, vol. 15/I, Georg Thieme Verlag, Stuttgart, 1974, (Abstract only).
Aluvila, S., et al., "Inhibitors of the Mitochondrial Citrate Transport Protein: Validation of the Role of Substrate Binding Residues and Discovery of the First Purely Competitive Inhibitor", Mol. Pharmacol., 2010, vol. 77(1), pp. 26-34.

(Continued)

*Primary Examiner* — Jeffrey H Murray
(74) *Attorney, Agent, or Firm* — McDonnell Boehnen Hulbert & Berghoff LLP

(57) ABSTRACT

Chromenopyridine-based compounds are provided. In one aspect, the present disclosure provides a method for treating cancer in a subject in need thereof, the method comprising administering a therapeutically effective amount of a chromenopyridine-based compound to the subject. A representative compound is 2,4-diamino-7,8-dimethoxy-5-((4-methoxyphenyl)thio)-5H-chromeno[2,3-b]pyridine-3-carbonitrile (Compound 1).

19 Claims, 9 Drawing Sheets

(56) References Cited

PUBLICATIONS

Boyd, M.R., and Paull, K.D., "Some Practical Considerations and Applications of the National Cancer Institute In Vitro Anticancer Drug Discovery Screen", Drug Development Research, 1995, vol. 34, pp. 91-109.
Grever, M.R., et al., "The National Cancer Institute: Cancer Drug Discovery and Development Program", Seminars in Oncology, 1992, vol. 19(6), pp. 622-638, (Abstract only).
Shoemaker, R.H., "The NCI60 Human Tumor Cell Line Anticancer Drug Screen", Nature Rev. Cancer, Oct. 2006, vol. 6, pp. 813-823.

\* cited by examiner

CHROMENOPYRIDINE-BASED COMPOUNDS AND METHODS OF MAKING AND USE THEREOF

CROSS-REFERENCE TO RELATED APPLICATIONS

This application claims the benefit of priority of U.S. Provisional Application No. 63/107,299, filed Oct. 29, 2020, and U.S. Provisional Application No. 63/252,359, filed Oct. 5, 2021, each of which is incorporated herein by reference in its entirety.

FIELD

The present disclosure provides chromenopyridine-based compounds for the treatment of diseases, such as cancer. Methods of making the chromenopyridine-based compounds and uses thereof of also disclosed.

BACKGROUND

A defining characteristic of metastasis is the compensatory but dysregulated metabolic hyperactivity that supplies the cells' incessant need for nutrients and persistently replenishes the molecular building blocks for tumorigenesis (DeBaradinis 2016; Pavlova 2016). Thus, key components of cell signaling pathways and intermediary metabolic pathways have become targets for pharmacologic cancer therapy. Cytoplasmic targets include the following: 1) mTOR (mechanistic target of rapamycin; a protein kinase with dual specificity that phosphorylates serine/threonine and tyrosine residues), PI3K (phosphatidylinositol-3-kinase), AKT (aka protein kinase B) pathways, and combinations thereof are directed toward suppression of cell proliferation versus differentiation (Hua 2019; Yang 2019); and 2) PMCT (plasma membrane citrate transporter, SLC13A5) (Sun 2010; Kopel 2020), fatty acid synthase, ATP-citrate lyase, and acetyl-CoA synthetase 2 (Koundouros 2020) are intended for inhibition of de novo lipogenesis. Mitochondrial targets include the following: 1) CTP (citrate transport protein, SLC25A1) and 2) HIF1α (transcription factor hypoxia-inducible factor 1α)-regulated genes that are integral to the TCA (tricarboxylic acid) cycle (Paredes 2021). At the intersection of the cells' signaling and metabolic pathways and essential to homeostasis is the metabolite citrate.

Citrate is a molecule that is central to cellular bioenergetics and its intracellular availability is maintained via a balance of anaplerosis within mitochondria and import from circulating plasma. As the sole carbon backbone source for all fatty acid, lipid, and triglyceride biosyntheses, citrate and its transporters are modulators of cell proliferation. Recent studies have focused on both the altered metabolism and oncogenic signaling to inhibit the proliferation of human carcinomas by silencing the expression or inhibiting the transport activity of SLC13A5 (Hua 2019; Yang 2019; Kopel 2020; Koundouros 2019; Poolsri 2018) that we had dubbed PMCT, and is also known as NaCT (sodium-dependent citrate transporter). In concert, inhibition of PMCT upregulates AMPK (AMP-activated protein kinase) resulting in the inhibition of lipogenesis, followed by the downstream effect of inhibiting mTORC1 (mTOR Complex 1) thus inhibiting protein synthesis (Li 2017). Cell proliferation, a hallmark of metastatic cancers, is characterized by hyperactivation of mTORC1, the more-studied of the two complexes comprising mTOR (aka mechanistic target of rapamycin), that is a key regulator of cell growth. The linkage of PMCT inhibition with both the AMPK-mTOR axis and PI3K/AKT/mTOR signaling pathway that is central to cell cycle regulation (i.e., mitogenesis, anabolism, catabolism, motility, quiescence, nutrient-sensing, autophagy, apoptosis) will be highly significant for cancer treatment. Despite the clear involvement of PMCT in metastasis, to date the therapeutic use of PMCT targeting with small molecules has not reached clinical trials. Thus, PMCT remains a key potential target for metabolic disease drug development and its inhibition potentially critical to cancer chemotherapy.

Hepatocellular carcinoma is an aggressive cancer, and the most common primary liver malignancy with a death rate ranking second among all cancers worldwide. Despite the progress that has been made in cancer treatment in recent years, cancer drug discovery remains highly challenging because of complicating factors such as tumor heterogeneity, toxicity, and acquired multidrug resistance (MDR). Therefore, the development of novel anticancer drugs with new mechanisms of action is crucial. The plasma membrane citrate transporter (PMCT) is a transport protein that is expressed predominantly in the liver in mammals. There, it functions as part of a variety of metabolic pathways including as a key regulator of glycolysis. Recent studies have shown that loss or inhibition of PMCT halts hepatocellular carcinoma cell growth by disrupting energy homeostasis, suggesting that PMCT could be a therapeutic target for treating cancer, including liver cancer. Novel molecular frameworks and approaches, including synthetic methods and methods of use, must be identified in order to advance drug discovery towards PMCT inhibition.

SUMMARY

The present disclosure concerns chromenopyridine-based compounds for the treatment of cancer. In particular, the plasma membrane citrate transporter has been identified as a candidate for drug inhibition towards treating particular cancers, such as hepatocellular carcinoma.

According, in one aspect, the present disclosure provides for a compound of formula (I):

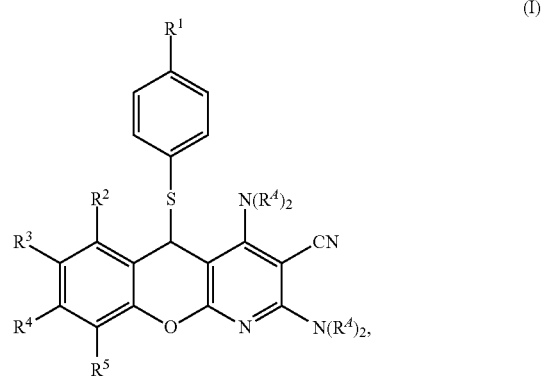

or a or a pharmaceutically acceptable salt thereof, wherein:
$R^1$ is —OH, —O—($C_1$-$C_4$ alkyl), or —S—($C_1$-$C_4$ alkyl);
$R^2$, $R^3$, and $R^5$ are each independently H, —OH, or —O—($C_1$-$C_6$ alkyl);
$R^4$ is —OH, ($C_1$-$C_2$ alkyl), —O—($C_1$-$C_6$ alkyl), or —N—($CH_2CH_3$)$_2$; and
each $R^4$ is independently H or $CH_3$.

In another aspect, the present disclosure provides for a method of treating cancer in a subject in need thereof, comprising administering a therapeutically effective amount of a compound as otherwise described herein to the subject.

In certain embodiments as otherwise described herein, the cancer is leukemia, non-small cell lung cancer, colon cancer, CNS cancer, melanoma, ovarian cancer, renal cancer, prostate cancer, or hepatocellular carcinoma.

Other aspects of the disclosure will be apparent to those skilled in the art in view of the description that follows.

DETAILED DESCRIPTION

Figure 1A:
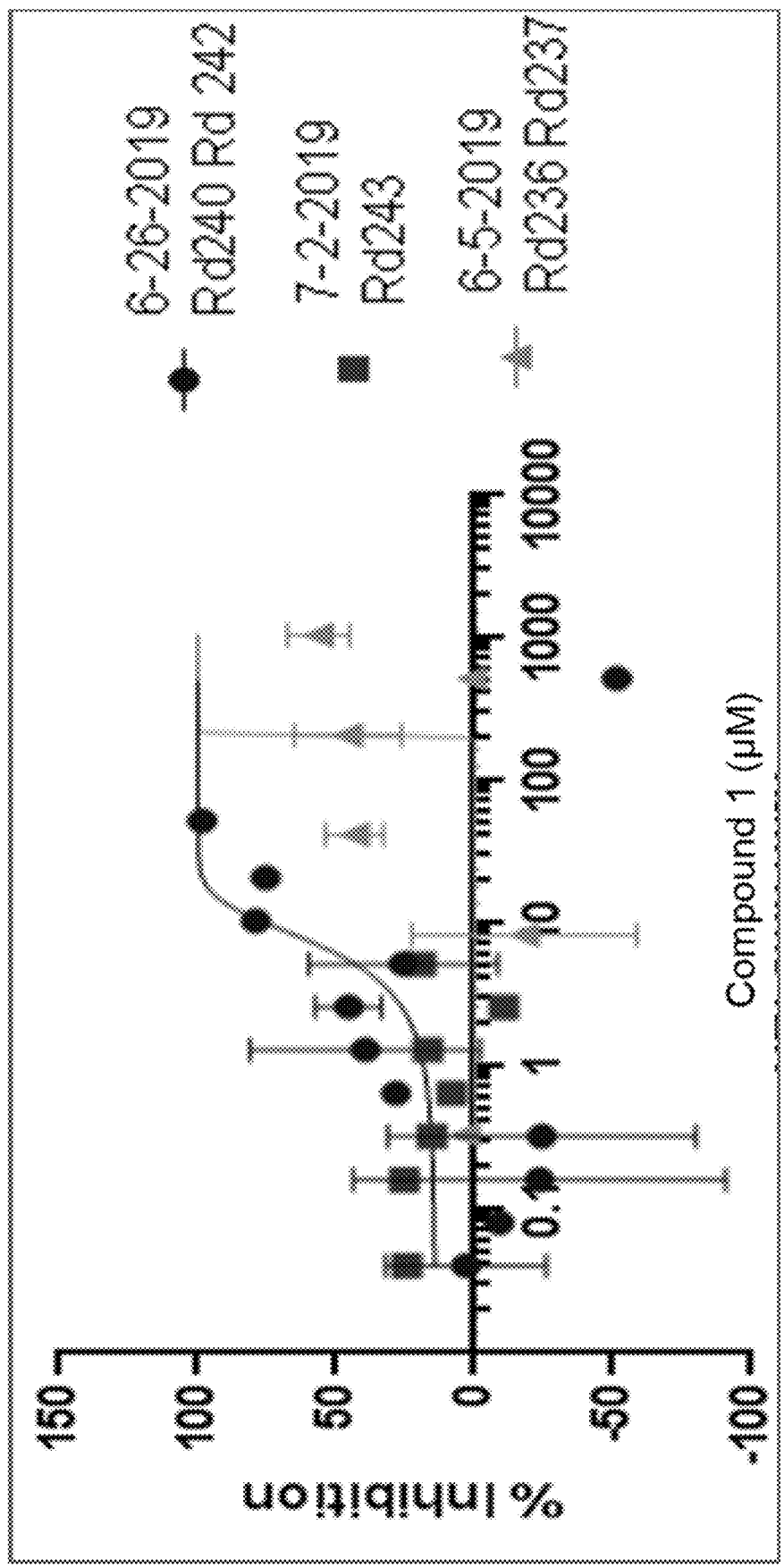
FIG. 1A and FIG. 1B display the dose-dependent inhibition of PMCT in HEK293T cells by Compound 1 according to an example embodiment.

The chromenopyridine moiety has been identified as a promising drug scaffold with a wide variety of biological activity. As described herein, novel chromenopyridines are synthesized using an efficient and modular procedure.

According, in one aspect, the present disclosure provides for a compound of formula (I):

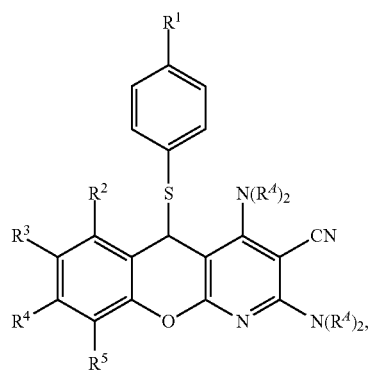

(I)

or a or a pharmaceutically acceptable salt thereof, wherein:
$R^1$ is —OH, —O—($C_1$-$C_4$ alkyl), or —S—($C_1$-$C_4$ alkyl);
$R^2$, $R^3$, and $R^5$ are each independently H, —OH, or —O—($C_1$-$C_6$ alkyl);
$R^4$ is —OH, ($C_1$-$C_2$ alkyl), —O—($C_1$-$C_6$ alkyl), or —N—$(CH_2CH_3)_2$; and
each $R^A$ is independently H or $CH_3$.

The compounds can be defined generically as with respect to formula (I), or in various subgenera formulae in which $R^1$, $R^2$, $R^3$, and $R^6$, and $R^5$ are optionally independently selected from the groups (1a) et seq., (2a) et seq., and (3a) et seq. defined herein below (e.g., wherein the compound is of a structural formula as defined in any combination of the embodiments below):

In certain embodiments of the compounds as otherwise described herein, $R^1$ is selected from the following groups (1a)-(1d):

(1a) —OH, —O—($C_1$-$C_2$ alkyl), or —S—($C_1$-$C_2$ alkyl);
(1b) —OH or —O—$CH_3$;
(1c) —O—$CH_3$;
(1d) —S—$CH_3$.

In certain embodiments of the compounds as otherwise described herein, $R^2$, $R^3$, and $R^5$ are selected from one of the following groups (2a)-(2c):

(2a) at least two of $R^2$, $R^3$, and $R^5$ are H;
(2b) as defined in (2a), wherein one of $R^2$, $R^3$, and $R^5$ is —OH, —$OCH_3$ or —O—$CH_2CH_3$;
(2c) as defined in (2a), wherein $R^2$ or $R^3$ is —$OCH_3$.

In certain embodiments of the compounds as otherwise described herein, $R^4$ is selected from one of the following groups (3a)-(3c):

(3a) —OH, —$CH_3$, —O—($C_1$-$C_4$ alkyl), or —N—$(CH_2CH_3)_2$;
(3b) —OH, —$CH_3$, —O—$CH_3$, or —N—$(CH_2CH_3)_2$;
(3c) —OH, —$CH_3$, or —O—$CH_3$;
(3d) —O—$CH_3$.

In certain embodiments as otherwise described herein, for example in embodiments (1a)-(3d) above, $R^4$ is not —N$(CH_2CH_3)_2$ when $R^1$ is —$OCH_3$ or —$SCH_3$.

In certain embodiments as otherwise described herein, for example in embodiments (1a)-(3d) above, $R^A$ is H or $CH_3$, for example, $R^A$ is H.

In certain embodiments as otherwise described herein, the compound is of formula (II):

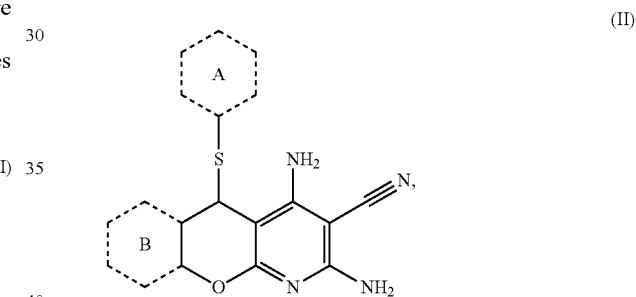

(II)

wherein:
A is

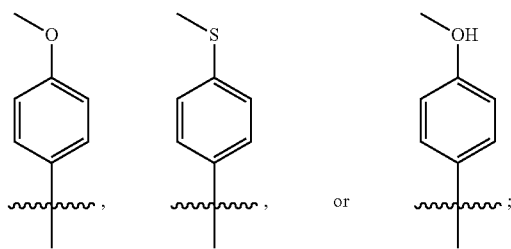

and
B is

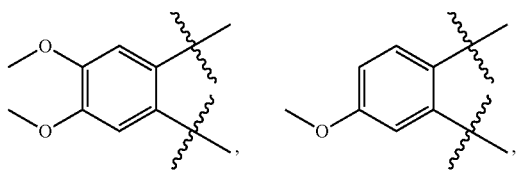

-continued

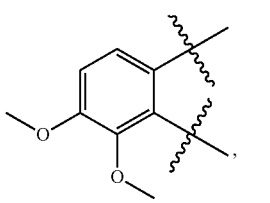,

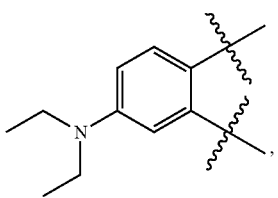,

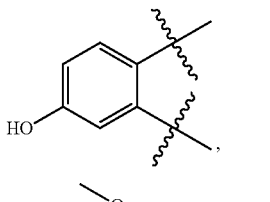, or

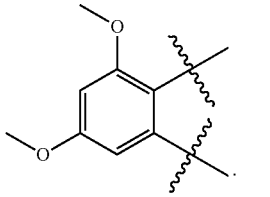.

In certain embodiments as otherwise described herein, with A is

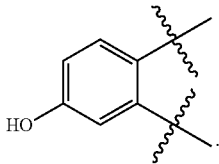 or , and B is

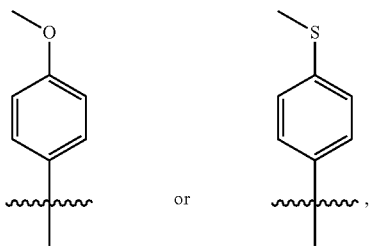,

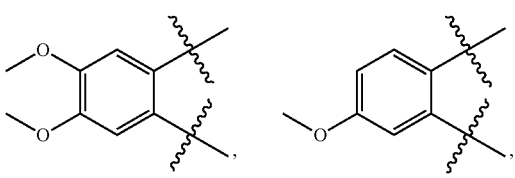,

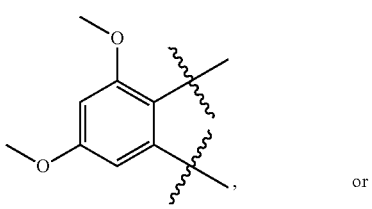 or

-continued

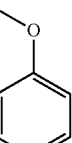

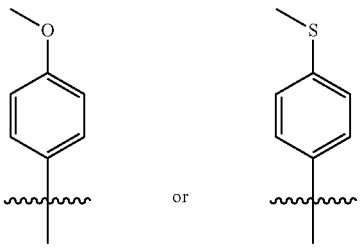.

For example, in particular embodiments, A is

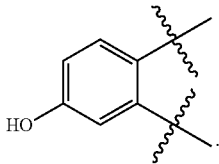 or , and B is

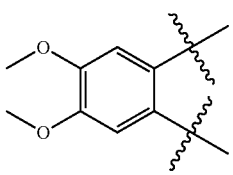 [SMILES: *c1cc(OC)c(OC)cc1*]

The compound according to the present disclosure may be neutral form, or may be a pharmaceutically acceptable salt thereof. For example, in certain embodiments as otherwise described herein, the compound may be a salt or ester or derivative. Examples of suitable salts include those formed with organic or inorganic acid, such as salts of acetate, tartrate, bitartrate, trifluoroacetate, lactate, maleate, fumarate, citrate, methanesulfonate, sulfate, phosphate, nitrate, or chloride.

In certain additional embodiments, including any of the embodiments described with reference to formula (I) above, each optionally substituted alkyl is unsubstituted.

A compound as described herein can usefully be provided in the form of a pharmaceutical composition. Such compositions include the compound according to any one of the preceding aspects or embodiments described herein, together with a pharmaceutically acceptable excipient, diluent, or carrier.

The compounds may be formulated in the pharmaceutical composition per se, or in the form of a hydrate, solvate, or pharmaceutically acceptable salt, as previously described. Typically, such salts are more soluble in aqueous solutions than the corresponding free acids and bases, but salts having lower solubility than the corresponding free acids and bases may also be formed.

The compound described herein may be administered by any suitable routes including, without limitation, orally, transdermally, intraveneously, or via inhalent in dosage unit formulations containing conventional non-toxic pharmaceutically acceptable carriers, adjuvants and vehicles. The pharmaceutical compositions described herein may be in a form suitable for administration such as oral use, for example, as tablets, troches, lozenges, aqueous or oily suspensions, dispersible powders or granules, emulsion, hard or soft capsules, or syrups or elixirs.

Compositions intended for oral use may be prepared according to any method known in the art for the manufacture of pharmaceutical compositions and such compositions may contain one or more agents selected from the group consisting of sweetening agents, flavoring agents, coloring agents and preservative agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques, for example with an enteric coating. In some cases such coatings may be prepared by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules, wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil. Formulations for oral use may also be presented as lozenges.

Aqueous suspensions contain the active materials in admixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

The methods of the present disclosure involve the administration of an effective dose of a compound to cancer in mammals such as humans. In certain embodiments as otherwise described herein, the compound can be administered in a daily amount ranging 0.1 mg/kg to 400 mg/kg, or 1 mg/kg to 400 mg/kg. For example, in certain embodiments, the compound can be administered in daily amount ranging from 5 mg/kg to 80 mg/kg. In other embodiments, the compound can be administered in a daily amount ranging from 10 mg/kg to 250 mg/kg, or 20 mg/kg to 250 mg/kg, or 40 mg/kg to 250 mg/kg. For example, in particular embodiments, the compound is administered in a daily amount in the range of 1 mg/kg to 150 mg/kg, for example, in the range of 2 mg/kg to 100 mg/kg, or 5 mg/kg to 80 mg/kg, or 5 mg/kg to 60 mg/kg, or 10 mg/kg to 50 mg/kg. It is to be understood that the milligram dosage quoted reflects the equivalent milligrams of pure thiol-containing compound (i.e., without inclusion of any anions or salts in the molecular weight).

In certain embodiments as otherwise described herein, the dose of the compound can be administered one or more times per day, such as one time per day, two times per day, three, four, or six times per day. In certain embodiments as otherwise described herein, the compound or the composition comprising the compound is administered for any suitable period of time. For example, the compound or the composition comprising the compound may be administered for a period of at least three weeks, or a period of 4-6 weeks, or for a period of at least 4 weeks, 6 weeks, 8 weeks, 12 weeks, or at least 24 weeks.

In another aspect, the present disclosure provides for a method of treating cancer in a subject in need thereof, comprising administering a therapeutically effective amount of a compound as otherwise described herein to the subject.

The compounds described herein have been identified as therapeutic candidates towards a variety of cancer. For example, in certain embodiments as otherwise described herein, the cancer is liver cancer such as hepatocellular carcinoma, leukemia, non-small cell lung cancer, colon cancer, CNS (central nervous system) cancer, melanoma, ovarian cancer, renal cancer, prostate cancer, breast cancer Definitions Terms used herein may be preceded and/or followed by a single dash, "-", or a double dash, "=", to indicate the bond order of the bond between the named substituent and its parent moiety; a single dash indicates a single bond and a double dash indicates a double bond or a pair of single bonds in the case of a spiro-substituent. In the absence of a single or double dash it is understood that a single bond is formed between the substituent and its parent moiety; further, substituents are intended to be read "left to right" with reference to the chemical structure referred to unless a dash indicates otherwise. For example, arylalkyl, arylalkyl-, and -alkylaryl indicate the same functionality.

For simplicity, chemical moieties are defined and referred to throughout primarily as univalent chemical moieties (e.g., alkyl, aryl, etc.). Nevertheless, such terms are also used to convey corresponding multivalent moieties under the appropriate structural circumstances clear to those skilled in the art. For example, while an "alkyl" moiety can refer to a monovalent radical (e.g., CH$_3$—CH$_2$—), in some circumstances a bivalent linking moiety can be "alkyl," in which case those skilled in the art will understand the alkyl to be a divalent radical (e.g., —CH$_2$—CH$_2$—), which is equivalent to the term "alkylene." (Similarly, in circumstances in which a divalent moiety is required and is stated as being "aryl," those skilled in the art will understand that the term "aryl" refers to the corresponding divalent moiety, arylene). All atoms are understood to have their normal number of valences for bond formation (i.e., 4 for carbon, 3 for N, 2 for O, and 2, 4, or 6 for S, depending on the oxidation state of the S). Nitrogens in the presently disclosed compounds can be hypervalent, e.g., an N-oxide or tetrasubstituted ammonium salt. On occasion a moiety may be defined, for example, as —B-(A)$_n$, wherein a is 0 or 1. In such instances, when a is 0 the moiety is —B and when a is 1 the moiety is —B-A.

As used herein, the term "alkyl" includes a saturated hydrocarbon having a designed number of carbon atoms, such as 1 to 10 carbons (i.e., inclusive of 1 and 10), 1 to 8 carbons, 1 to 6 carbons, 1 to 3 carbons, or 1, 2, 3, 4, 5 or 6.

Alkyl group may be straight or branched and depending on context, may be a monovalent radical or a divalent radical (i.e., an alkylene group). For example, the moiety "—($C_1$-$C_6$ alkyl)-O—" signifies connection of an oxygen through an alkylene bridge having from 1 to 6 carbons and $C_1$-$C_3$ alkyl represents methyl, ethyl, and propyl moieties. Examples of "alkyl" include, for example, methyl, ethyl, propyl, isopropyl, butyl, iso-, sec- and tert-butyl, pentyl, and hexyl.

The terms "halogen" or "halo" indicate fluorine, chlorine, bromine, and iodine. In certain embodiments of each and every embodiment as otherwise described herein, the term "halogen" or "halo" refers to fluorine or chlorine. In certain embodiments of each and every embodiment described herein, the term "halogen" or "halo" refers to fluorine. The term "fluoroalkyl" indicates an alkyl group (i.e., as otherwise described herein) that is substituted with at least one fluorine. "Fluoroalkyl" or "fluorinated alkyl" includes alkyl groups substituted with one or multiple fluorines, such as perfluoroalkyl groups. Examples of fluoroalkyl groups include fluoromethyl, difluoromethyl, trifluoromethyl, pentafluoroethyl, 2,2,2-trifluoroethyl, 1,1,1,3,3,3-hexafluoroprop-2-yl and 2,2,3,3,3-pentafluoroprop-1-yl.

The term "oxo" means a doubly bonded oxygen, sometimes designated as =O or for example in describing a carbonyl "C(O)" may be used to show an oxo substituted carbon.

The term "substituted," when used to modify a specified group or radical, means that one or more hydrogen atoms of the specified group or radical are each, independently of one another, replaced with the same or different substituent groups as defined below, unless specified otherwise.

As used herein, the phrase "pharmaceutically acceptable salt" refers to both pharmaceutically acceptable acid and base addition salts and solvates. Such pharmaceutically acceptable salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, HOOC—$(CH_2)_n$—COOH where n is 0-4, and the like. Non-toxic pharmaceutical base addition salts include salts of bases such as sodium, potassium, calcium, ammonium, and the like. Those skilled in the art will recognize a wide variety of non-toxic pharmaceutically acceptable addition salts.

One of ordinary skill in the art of medicinal chemistry also will appreciate that the disclosed structures are intended to include isotopically enriched forms of the present compounds. As used herein "isotopes" includes those atoms having the same atomic number but different mass numbers. As is known to those of skill in the art, certain atoms, such as hydrogen occur in different isotopic forms. For example, hydrogen includes three isotopic forms, protium, deuterium and tritium. As will be apparent to those of skill in the art upon consideration of the present compounds, certain compounds can be enriched at a given position with a particular isotope of the atom at that position. For example, compounds having a fluorine atom, may be synthesized in a form enriched in the radioactive fluorine isotope $^{18}F$. Similarly, compounds may be enriched in the heavy isotopes of hydrogen: deuterium and tritium; and similarly can be enriched in a radioactive isotope of carbon, such as $^{13}C$. Such isotopic variant compounds undergo different metabolic pathways and can be useful, for example, in studying the ubiquitination pathway and its role in disease. Of course, in certain embodiments, the compound has substantially the same isotopic character as naturally-occurring materials.

One of ordinary skill in the art of chemistry will also appreciate that the disclosed structures, unless otherwise indicated are intended to include all possible stereoisomers of the claimed molecule, including mixtures of certain or all stereoisomers. However, compounds drawn with certain stereochemistry at one or more stereocenters are intended to have the indicated stereochemistry. Compounds and stereocenters drawn with ambiguous stereochemistry are meant to convey any stereoisomer or mixture thereof, e.g., a racemic mixture of compounds or a purified subset of stereoisomers.

As used herein, the terms "individual," "patient," or "subject" are used interchangeably, refers to any animal, including mammals, preferably humans.

As used herein, the phrase "therapeutically effective amount" or "effective amount" refers to the amount of active compound or pharmaceutical agent that elicits the biological or medicinal response that is being sought in a tissue, system, animal, individual or human by a researcher, veterinarian, medical doctor or other clinician.

Examples of methods and systems are described herein. It should be understood that the words "exemplary," "example," and "illustrative," are used herein to mean "serving as an example, instance, or illustration." Any embodiment or feature described herein as "exemplary," "example," or "illustrative," is not necessarily to be construed as preferred or advantageous over other embodiments or features. Further, the exemplary embodiments described herein are not meant to be limiting. It will be readily understood that certain aspects of the disclosed systems and methods can be arranged and combined in a wide variety of different configurations.

EXAMPLES

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Compounds as described herein can be purified by any of the means known in the art, including chromatographic means, such as HPLC, preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as J. F. W. McOmie, "Protective Groups in Organic Chemistry," Plenum Press, London and New York 1973, in T. W. Greene and P. G. M. Wuts, "Protective Groups in Organic Synthesis," Third edition, Wiley, New York 1999, in "The Peptides"; Volume 3 (editors: E. Gross and J. Meienhofer), Academic Press, London and New York 1981, in "Methoden der organischen Chemie," Houben-Weyl, 4.sup.th edition, Vol. 15/1, Georg Thieme Verlag, Stuttgart 1974, in H.-D. Jakubke and H. Jescheit, "Aminosauren, Peptide, Proteine," Verlag Chemie, Weinheim, Deerfield Beach, and Basel 1982, and/or in Jochen Lehmann, "Chemie der Kohlenhydrate: Monosaccharide and Derivate," Georg Thieme Verlag, Stuttgart 1974. The protecting groups may be removed at a convenient subsequent stage using methods known from the art.

The compounds disclosed herein can be made using procedures familiar to the person of ordinary skill in the art and as described herein, for example in Scheme 1. One of skill in the art can adapt the reaction sequences of schemes and examples as provided herein to fit the desired target molecule. Of course, in certain situations one of skill in the art will use different reagents to affect one or more of the individual steps or to use protected versions of certain of the substituents. Additionally, one skilled in the art would recognize that compounds of the disclosure can be synthesized using different routes altogether. For example, the person of ordinary skill in the art may adapt the procedures described herein and/or other procedures familiar to the person of ordinary skill in the art to make the compounds described herein.

Example 1: Compound Preparation

Scheme 1. Synthesis of new chromenopyridines

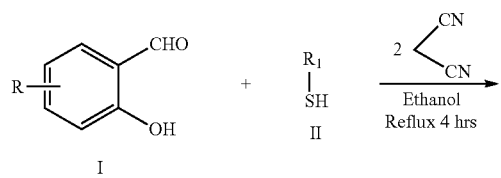

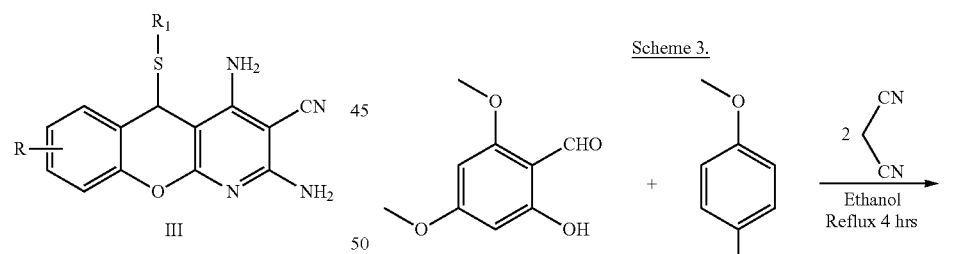

R = OCH₃, R₁ = Substituted phenyl

General Procedure for Preparation of Chromenopyridine Analogs

Two mmole of malononitrile, 1 mmol of the desired substituted thiophenol and 0.1 mmol of trimethylamine was added to a solution of 1 mmol substituted salicylaldehyde in 7 mL ethanol. The resulting reaction mixture was allowed to reflux for 4 hours, at which point the product precipitated out of the solution. The precipitate was filtered and dried under reduced pressure, and then further purified by dissolution in DMF (3 mL), filtration, and precipitation with water (4 mL). The purified precipitate was filtered and dried under reduced pressure leading to the pure substituted 5-arylthio-5H-chromenopyridine as light red to light yellow solids.

Preparation of Compound 1

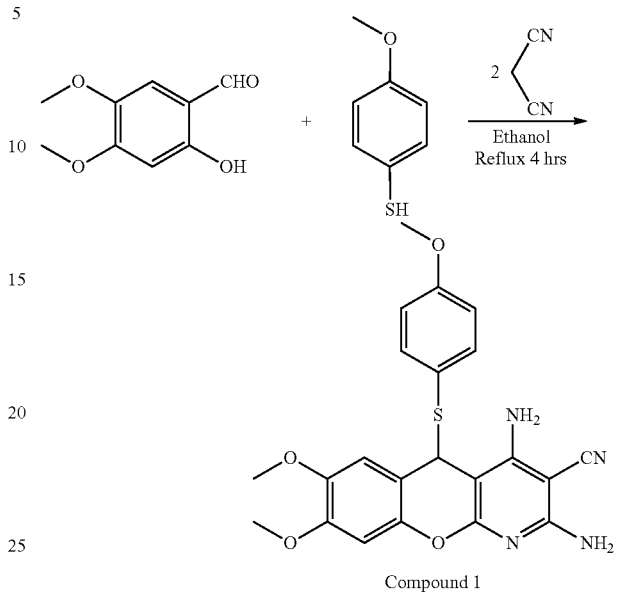

Compound 1

The above general procedure was employed with 4-methoxybenzene thiol as the substituted thiophenol, and 2-hydroxy-4,5-dimethoxybenzaldehyde as the substituted salicylaldehyde, yielding a yellowish white solid. $^1$H NMR (300 MHz, DMSO-$d_6$): δ 6.84 (bs, 2H), 6.78 (d, J=9.0 Hz, 2H), 6.72 (d, J=9.0 Hz, 2H), 6.48 (s, 1H), 6.45 (d, J=6.0 Hz, 2H), 5.56 (s, 1H), 3.71 (s, 3H), 3.70 (s, 3H), 3.62 (s, 3H); $^{13}$C-NMR (DMSO-$d_6$, 75.4 MHz): 160.4, 159.9, 150.8, 149.3, 145.4, 138.1, 122.2, 117.1, 114.3, 112.6, 110/9, 100.4, 86.7, 70.7, 56.1, 55.6, 43.7 ppm; MS (MeOH): 297.3, consistent with C—S cleavage; Anal. Calcd. For $C_{22}H_{20}N_4O_4S$.

Preparation of Compound 2

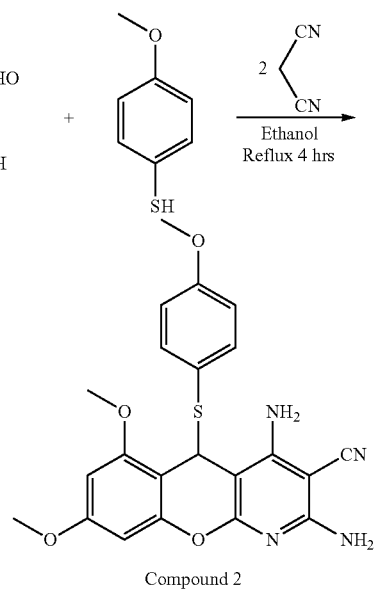

Compound 2

Compound 2 (2,4-diamino-6,8-dimethoxy-5-((4-methoxyphenyl)thio)-5H-chromeno[2,3-b]pyridine-3-carbonitrile) was prepared as follows: 2 mmol of malononitrile, 1 mmol of 4-methoxy-thiophenol and 0.1 mmol of triethyl amine was added to a solution of 1 mmol 2-hydroxy-4,6-dimethoxybenzaldehyde in 7 mL ethanol. The resulting reaction mixture was allowed to reflux for 4 hours, at which point the product precipitates out of the solution. The resulting precipitate was filtered off and dried under vacuum. The residue was further purified by dissolution in DMF (3 mL), filtration, and precipitation of the product with water (4 mL). The precipitate was filtered off and dried under vacuum leading to the pure Compound 2 as yellowish white solid. The purified compound has been characterized by $^1$H NMR, $^{13}$C{$^1$H} NMR and mass spectrometry. $^1$H NMR (600 MHz, DMSO-d$_6$): δ 6.86 (s, 2H), 6.65 (d, J=12.0 Hz, 2H), 6.65 (d, J=6.0 Hz, 2H), 6.38 (bs, 3H), 6.01 (s, 1H), 5.55 (s, 1H), 3.85 (s, 3H), 3.74 (s, 3H), 3.69 (s, 3H); MS (MeOH): 297.3 and 319.3 (+Na) (consistent with C—S cleavage); Anal. Calcd. For C$_{22}$H$_{20}$N$_4$O$_4$S.

Preparation of Compound 3

Scheme 4.

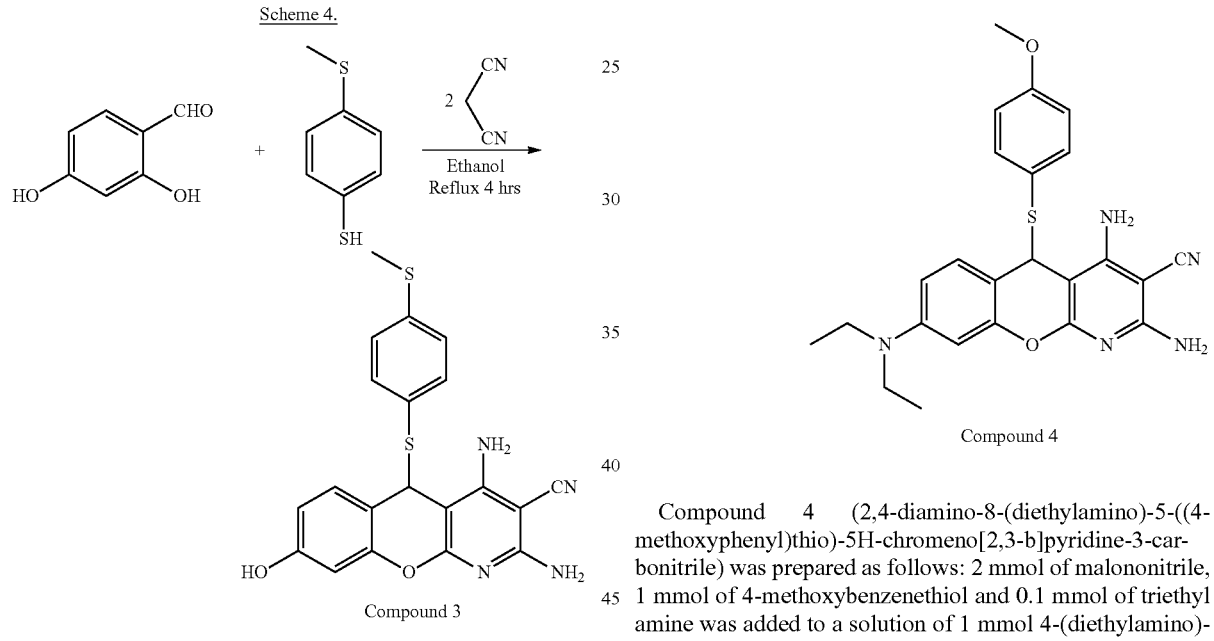

Compound 3

Compound 3 (2,4-Diamino-8-hydroxy-5-((4-(methylthio) phenyl)thio)-5H-chromeno[2,3-b]pyridine-3-carbonitrile) was prepared as follows: 2 mmol of malononitrile, 1 mmol of 4-(methylthio)benzenethiol and 0.1 mmol of triethyl amine was added to a solution of 1 mmol 2,4-dihydroxybenzaldehyde in 7 mL ethanol. The resulting reaction mixture was allowed to reflux for 4 hours, at which point the product precipitates out of the solution. The resulting precipitate was filtered off and dried under vacuum. The residue was further purified by dissolution in DMF (3 mL), filtration, and precipitation of the product with water (4 mL). The precipitate was filtered off and dried under vacuum leading to the pure Compound 3 as yellowish white solid. The purified compound has been characterized by $^1$H NMR, $^{13}$C{$^1$H} NMR and mass spectrometry. $^1$H NMR (300 MHz, DMSO-d$_6$): δ 9.68 (s, 1H), 7.00 (d, J=9.0 Hz, 3H), 6.88 (bs, 2H), 6.69 (d, J=9.0 Hz, 2H), 6.56-6.46 (m, 3H), 6.20 (s, 1H), 5.61 (s, 1H), 2.42 (s, 3H); MS (MeOH): 407.2 and 252.7 (consistent with C—S cleavage); Anal. Calcd. For C$_{20}$H$_{16}$N$_4$O$_2$S$_2$.

Preparation of Compound 4

Scheme 5.

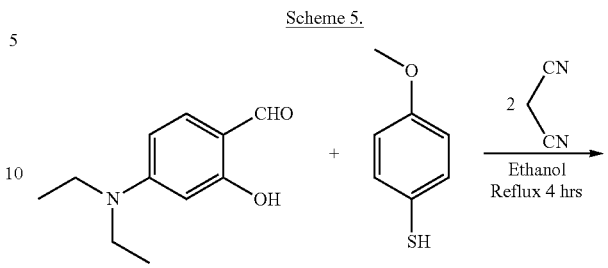

Compound 4

Compound 4 (2,4-diamino-8-(diethylamino)-5-((4-methoxyphenyl)thio)-5H-chromeno[2,3-b]pyridine-3-carbonitrile) was prepared as follows: 2 mmol of malononitrile, 1 mmol of 4-methoxybenzenethiol and 0.1 mmol of triethyl amine was added to a solution of 1 mmol 4-(diethylamino)-2-hydroxybenzaldehyde in 7 mL ethanol. The resulting reaction mixture was allowed to reflux for 4 hours, at which point the product precipitates out of the solution. The resulting precipitate was filtered off and dried under vacuum. The residue was further purified by dissolution in DMF (3 mL), filtration, and precipitation of the product with water (4 mL). The precipitate was filtered off and dried under vacuum leading to the pure Compound 4 as a red solid. The purified compound has been characterized by $^1$H NMR, $^{13}$C{$^1$H} NMR and mass spectrometry. Yield 39%; $^1$H NMR (300 MHz, DMSO-d$_6$): δ 1.07 (t, J=6.0 Hz, 6H), 3.32 (q, 4H merged with DMSO water peak), 3.66 (s, 3H), 5.52 (s, 1H), 6.00 (d, J=3.0 Hz, 1H), 6.35 (bs, 2H), 6.46 (dd, J=3.0 Hz, 1H), 6.65-6.68 (m, 3H), 6.76 (bs, 2H), 6.95 (d, J=6.0 Hz, 2H); $^{13}$C-NMR (DMSO-d6, 75.4 MHz): 159.8, 159.7, 159.3, 156.2, 152.2, 147.6, 137.7, 129.3, 121.9, 116.6, 113.6, 108.1, 107.9, 97.6, 87.5, 70.1, 55.1, 43.7, 43.2, 12.4 ppm; MS (MeOH): 308.1, consistent with C—S cleavage; Anal. Calcd. (C$_{24}$H$_{25}$N$_5$O$_2$S): C, 64.41; H, 5.63; N, 15.65. Found: C, 63.98; H, 5.49; N, 15.67.

Preparation of Compound 5

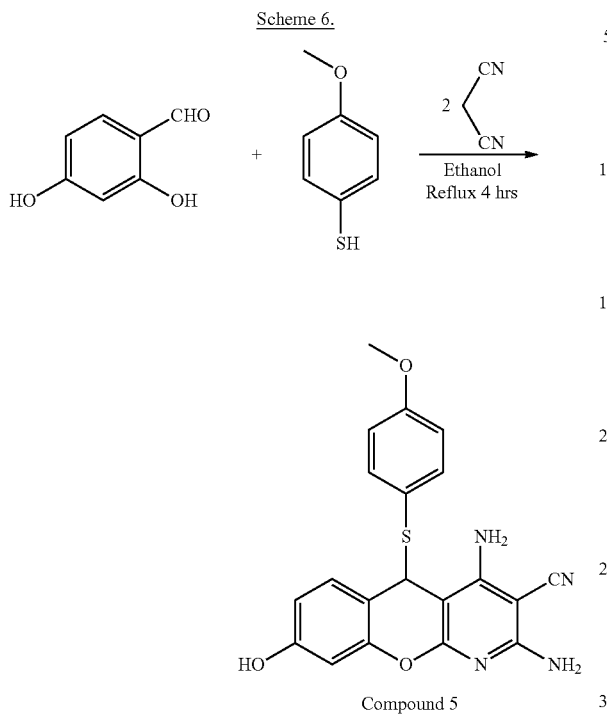

Compound 5

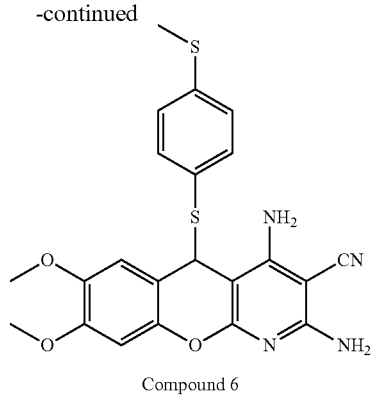

Compound 5 (2,4-Diamino-8-hydroxy-5-(((4-methoxyphenyl)thio)-5H-chromeno[2,3-b]pyridine-3-carbonitrile) was prepared as follows: 2 mmol of malononitrile, 1 mmol of 4-methoxybenzenethiol and 0.1 mmol of triethyl amine was added to a solution of 1 mmol 2,4-dihydroxybenzaldehyde in 7 mL ethanol. The resulting reaction mixture was allowed to reflux for 4 hours, at which point the product precipitates out of the solution. The resulting precipitate was filtered off and dried under vacuum. The residue was further purified by dissolution in DMF (3 mL), filtration, and precipitation of the product with water (4 mL). The precipitate was filtered off and dried under vacuum leading to the pure Compound 5 as yellowish white solid. The purified compound has been characterized by $^1$H NMR, $^{13}$C{$^1$H} NMR and mass spectrometry. $^1$H NMR (300 MHz, DMSO-d$_6$): δ 9.65 (s, 1H), 6.98 (d, J=9.0 Hz, 1H), 6.84 (bs, 2H), 6.71-6.64 (m, 4H), 6.56-6.53 (m, 1H), 6.43 (bs, 2H), 6.18 (s, 1H), 5.54 (s, 1H), 3.70 (s, 3H); MS (MeOH): 391.6 and 252.3 (consistent with C—S cleavage); Anal. Calcd. For C$_{20}$H$_{16}$N$_4$O$_3$S.

Preparation of Compound 6

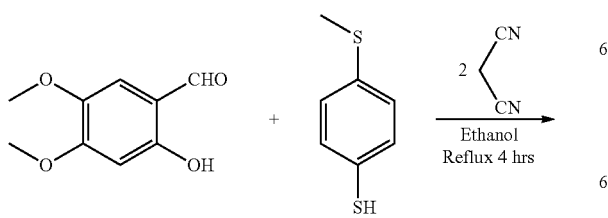

Compound 6

Compound 6 (2,4-diamino-7,8-dimethoxy-5-((4-(methylthio)phenyl)thio)-5H-chromeno[2,3-b]pyridine-3-carbonitrile) was prepared as follows: 2 mmol of malononitrile, 1 mmol of 4-(methylthio)benzenethiol and 0.1 mmol of triethyl amine was added to a solution of 1 mmol 2-hydroxy-4,5-dimethoxybenzaldehyde in 7 mL ethanol. The resulting reaction mixture was allowed to reflux for 4 hours, at which point the product precipitates out of the solution. The resulting precipitate was filtered off and dried under vacuum. The residue was further purified by dissolution in DMF (3 mL), filtration, and precipitation of the product with water (4 mL). The precipitate was filtered off and dried under vacuum leading to the pure Compound 6 as yellowish white solid. The purified compound has been characterized by $^1$H NMR, $^{13}$C{$^1$H} NMR and mass spectrometry. $^1$H NMR (300 MHz, DMSO-d$_6$): δ 7.04 (d, J=9.0 Hz, 2H), 6.89-682 (m, 4H), 6.52-6.44 (m, 4H), 5.64 (s, 1H), 3.72 (s, 3H), 3.61 (s, 3H), 2.43 (s, 3H); MS (MeOH): 450.2 and 296.5 (consistent with C—S cleavage); Anal. Calcd. For C$_{22}$H$_{20}$N$_4$O$_3$S$_2$.

Preparation of Compound 7

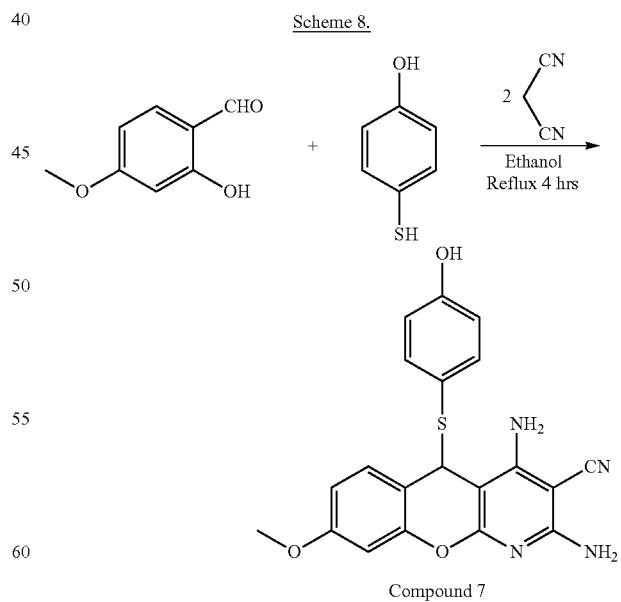

Compound 7

Compound 7 (2,4-Diamino-5-((4-hydroxyphenyl)thio)-8-methoxy-5H-chromeno[2,3-b]pyridine-3-carbonitrile) was prepared as follows: 2 mmol of malononitrile, 1 mmol of 4-mercaptophenol and 0.1 mmol of triethyl amine was added to a solution of 1 mmol 2-hydroxy-4-methoxybenzaldehyde in 7 mL ethanol. The resulting reaction mixture was allowed to reflux for 4 hours, at which point the product precipitates out of the solution. The resulting precipitate was filtered off and dried under vacuum. The residue was further purified by dissolution in DMF (3 mL), filtration, and precipitation of the product with water (4 mL). The precipitate was filtered off and dried under vacuum leading to the pure Compound 7 as yellowish white solid. The purified compound has been characterized by $^1$H NMR, $^{13}$C{$^1$H} NMR and mass spectrometry. $^1$H NMR (300 MHz, DMSO-d$_6$): δ 9.60 (s, 1H), 7.08 (d, J=9.0 Hz, 2H), 6.83 (bs, 2H), 7.00-6.92 (m, 3H), 6.86 (bs, 2H), 6.73-6.70 (m, 1H), 6.53-6.37 (m, 5H), 5.52 (s, 1H), 3.72 (s, 3H); MS (MeOH): 392.0 and 265.96 (consistent with C—S cleavage); Anal. Calcd. For $C_{20}H_{16}N_4O_3S$.

Preparation of Compound 8

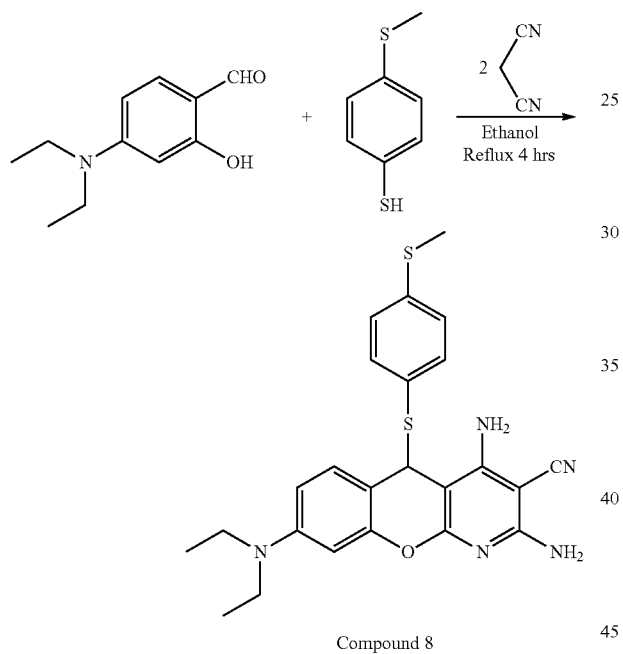

Compound 8

Compound 8 (2,4-diamino-8-(diethylamino)-5-((4-(methylthio)phenyl)thio)-5H-chromeno[2,3-b]pyridine-3-carbonitrile) was prepared as follows: 2 mmol of malononitrile, 1 mmol of 4-(methylthio)benzenethiol and 0.1 mmol of triethyl amine was added to a solution of 1 mmol 4-(diethylamino)-2-hydroxybenzaldehyde in 7 mL ethanol. The resulting reaction mixture was allowed to reflux for 4 hours, at which point the product precipitates out of the solution. The resulting precipitate was filtered off and dried under vacuum. The residue was further purified by dissolution in DMF (3 mL), filtration, and precipitation of the product with water (4 mL). The precipitate was filtered off and dried under vacuum leading to the pure Compound 8 as red solid. The purified compound has been characterized by $^1$H NMR, $^{13}$C{$^1$H} NMR and mass spectrometry. Yield 45%; $^1$H NMR (300 MHz, DMSO-d$_6$): δ 1.07 (t, J=6.0 Hz, 6H), 2.41 (s, 3H), 3.32 (q, 4H merged with DMSO water peak), 5.60 (s, 1H), 6.02 (s, 1H), 6.35 (bs, 2H), 6.38 (d, J=6.0 Hz, 1H), 6.73 (d, J=6.0 Hz, 2H), 6.80 (s, 1H), 6.97 (d, J=6.0 Hz, 2H), 7.27 (d, J=6.0 Hz, 1H), 7.44 (d, J=6.0 Hz, 1H); $^{13}$C-NMR (DMSO-d6, 75.4 MHz): 160.0, 159.5, 156.2, 152.3, 147.6, 139.1, 138.8, 136.4, 131.8, 129.1, 127.2, 126.6, 125.0, 116.6, 108.2, 107.8, 97.5, 87.2, 70.2, 43.8, 43.4, 14.5, 14.3, 12.2 ppm; MS (MeOH): 308.1 (consistent with C—S cleavage); Anal. Calcd. ($C_{24}H_{25}N_5OS_2 \cdot 0.5DMF$): C, 61.30; H, 5.73; N, 15.39. Found: C, 61.20; H, 5.25; N, 14.57.

Preparation of Compound 9

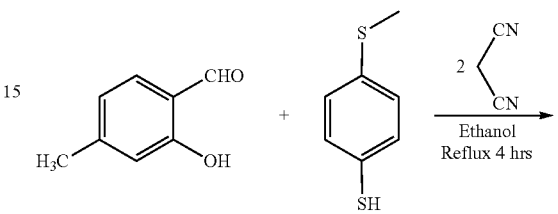

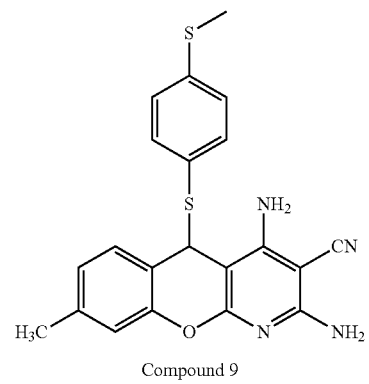

Compound 9

Compound 9 (2,4-Diamino-8-methyl-5-((4-(methylthio)phenyl)thio)-5H-chromeno[2,3-b]pyridine-3-carbonitrile) was prepared as follows: 2 mmol of malononitrile, 1 mmol of 4-(methylthio)benzenethiol and 0.1 mmol of triethyl amine was added to a solution of 1 mmol 2-hydroxy-4-methylbenzaldehyde in 7 mL ethanol. The resulting reaction mixture was allowed to reflux for 4 hours, at which point the product precipitates out of the solution. The resulting precipitate was filtered off and dried under vacuum. The residue was further purified by dissolution in DMF (3 mL), filtration, and precipitation of the product with water (4 mL). The precipitate was filtered off and dried under vacuum leading to the pure SAP-187(193) as yellowish white solid. The purified compound has been characterized by $^1$H NMR, $^{13}$C{$^1$H} NMR and mass spectrometry. $^1$H NMR (300 MHz, DMSO-d$_6$): δ 7.07-6.98 (m, 3H), 6.94-6.91 (m, 3H), 6.73-6.67 (m, 3H), 6.50 (bs, 2H), 5.68 (s, 1H), 2.42 (s, 3H), 2.27 (s, 3H); MS (MeOH): 404.9 and 250.2 (consistent with C—S cleavage); Anal. Calcd. For $C_{21}H_{18}N_4OS_2$.

The compounds shown below in Table 1 can be prepared essentially according to procedures known to those of skill in the art in view of the foregoing Example and Schemes 1-10.

TABLE 1
| Comp. No. | Name | Structure |
|---|---|---|
| 1 | 2,4-diamino-7,8-dimethoxy-5-((4-methoxyphenyl)thio)-5H-chromeno[2,3-b]pyridine-3-carbonitrile | 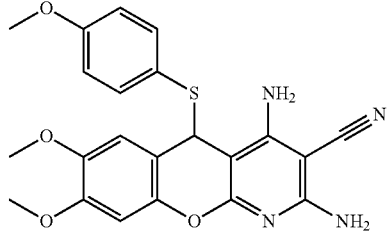 [SMILES: COc1ccc(SC2c3cc(OC)c(OC)cc3Oc3nc(N)c(C#N)c(N)c32)cc1] |
| 2 | 2,4-diamino-6,8-dimethoxy-5-((4-methoxyphenyl)thio)-5H-chromeno[2,3-b]pyridine-3-carbonitrile | 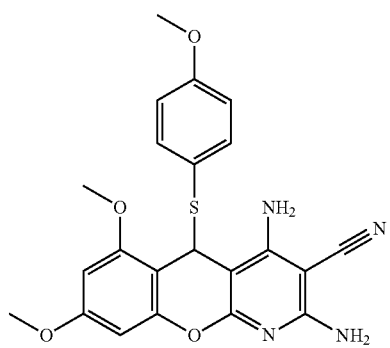 [SMILES: COc1ccc(SC2c3c(OC)cc(OC)cc3Oc3nc(N)c(C#N)c(N)c32)cc1] |
| 3 | 2,4-diamino-8-hydroxy-5-((4-(methylthio)phenyl)thio)-5H-chromeno[2,3-b]pyridine-3-carbonitrile | 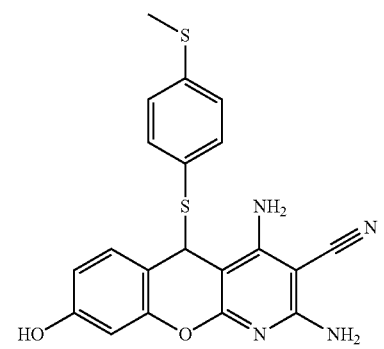 |
| 4 | 2,4-diamino-8-(diethylamino)-5-((4-methoxyphenyl)thio)-5H-chromeno[2,3-b]pyridine-3-carbonitrile | 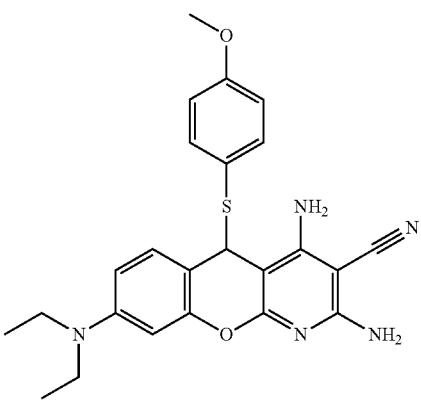 [SMILES: CCN(CC)c1ccc2c(c1)Oc1nc(N)c(C#N)c(N)c1C2Sc1ccc(OC)cc1] |

TABLE 1-continued

| Comp. No. | Name | Structure |
|---|---|---|
| 5 | 2,4-diamino-8-hydroxy-5-((4-methoxyphenyl)thio)-5H-chromeno[2,3-b]pyridine-3-carbonitrile | 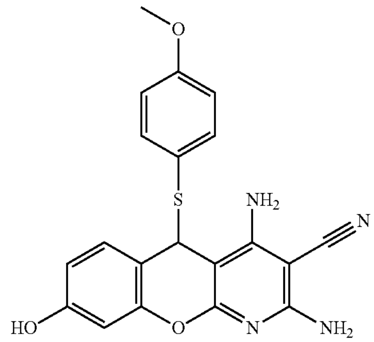 [SMILES: COc1ccc(SC2c3ccc(O)cc3Oc3nc(N)c(C#N)c(N)c32)cc1] |
| 6 | 2,4-diamino-7,8-dimethoxy-5-((4-(methylthio)phenyl)thio)-5H-chromeno[2,3-b]pyridine-3-carbonitrile | 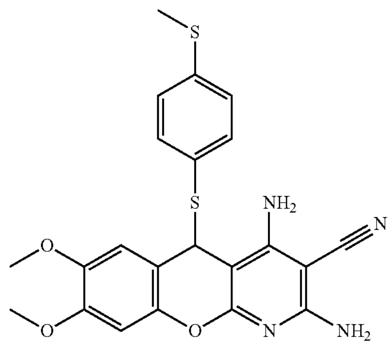 [SMILES: COc1cc2c(cc1OC)C(Sc1ccc(SC)cc1)c1c(nc(N)c(C#N)c1N)O2] |
| 7 | 2,4-diamino-5-((4-hydroxyphenyl)thio)-8-methoxy-5H-chromeno[2,3-b]pyridine-3-carbonitrile | 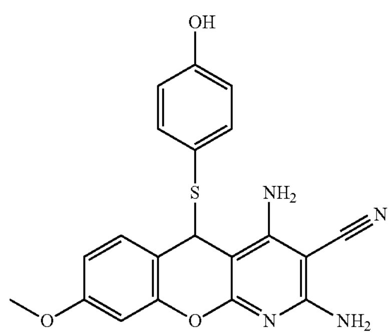 [SMILES: COc1ccc2c(c1)Oc1nc(N)c(C#N)c(N)c1C2Sc1ccc(O)cc1] |
| 8 | 2,4-diamino-8-(diethylamino)-5-((4-(methylthio)phenyl)thio)-5H-chromeno[2,3-b]pyridine-3-carbonitrile | 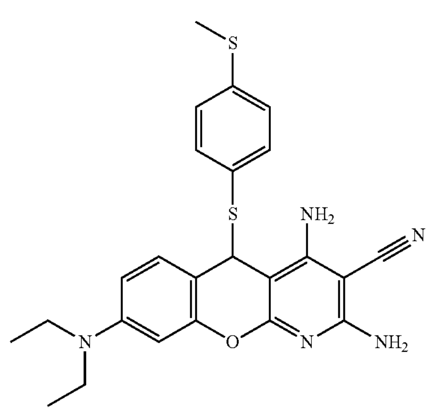 [SMILES: CCN(CC)c1ccc2c(c1)Oc1nc(N)c(C#N)c(N)c1C2Sc1ccc(SC)cc1] |

TABLE 1-continued

| Comp. No. | Name | Structure |
|---|---|---|
| 9 | 2,4-diamino-8-methyl-5-((4-(methylthio)phenyl)thio)-5H-chromeno[2,3-b]pyridine-3-carbonitrile | 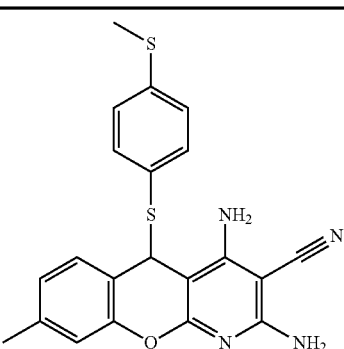 |

Example 2: PMCT Inhibition of Compounds 1-9

The inhibition of PMCT by Compounds 1-9 was tested using human HEK293T cells. This plasma membrane transporter mediates the preferential entry of citrate into cells from circulating blood, in which citrate concentration is at its highest, and was cloned from the human hepatoma cell line HepG2 cDNA library. In particular, the SLC13A5 (PMCT) gene was recombineered at the XhoI (5'-end) and XbaI (3'-end) cloning sites of the expression vector pcDNA3.1(+). The CMV (cytomegalovirus) promoter-controlled pcDNA3.1(+) expression plasmid and the HEK293T (human embryonic kidney) cell line combined to enable reproducible and robust citrate uptake.

Cell Culture of HEK293T

HEK293T cells, 293 [HEK293] (ATCC® CRL1573™), were cultured as prescribed by the ATCC (American Type Culture Collection) in the growth medium DMEM (Dulbecco's Modified Eagle Medium; Gibco 11995-065) supplemented with 10% (v/v) FBS (heat-inactivated fetal bovine serum; Gemini Bio-Products 100-106) and 1% (v/v) ABAM (antibiotic, anti-mitotic; Gibco 15240-062). At viable passages ranging from 11 to 21, HEK293T cells in 15×15 cm culture plates, each at 50-75% confluence (1-1.5×10$^7$ cells), were transfected with recombinant plasmid using PEI (polyethylenimine; Polysciences 23966-100). After 18 h of growth, cells were harvested as follows: 1) detachment via Trypsin-EDTA (Gibco 12604-013) confined to 3 m; 2) centrifugation at 300 g, 4 m, room temperature; 3) resuspension in fresh DMEM without supplements to dilute the Trypsin-EDTA; 4) combining of cell suspensions; 5) removal of aliquots for cell counting; 6) centrifugation as before to arrive at the final cell pellet; and 7) adjustment to an initial cell density of ~1 g/ml with fresh DMEM (no supplements). After a cell count is determined, the cells are suspended to a density of 6-9×10$^7$ cells/ml immediately before the transport assay.

Citrate Transport Assay of Whole Cells

The transport assay is conducted essentially as described previously (Nie R, Stark S, Symersky J, Kaplan R S, Lu M. "Structure and function of the divalent anion/Na+ symporter from *Vibrio cholerae* and a humanized variant." *Nat Commun.* 2017 Apr. 24; 8:15009) except as follows: 1) Live cells are pipetted with wide-bore tips only. 2) Live cells are maintained on ice until 1 m before addition of either H$_2$O or NEM (N-ethylmaleimide; Sigma-Aldrich E1271). 3) At uptake, the extracellular milieu of a sample reaction consists of ~233 mM Na$^+$+2.0 mM $^{12,14}$C-citrate+3.4 mM K$^+$+24 mM other DMEM components; the intracellular composition is ~157 mM Na$^+$+5.3 mM K$^+$+38 mM other DMEM components, thus creating a Na$^+$ concentration gradient that is ~1.5:1 out—versus inside the cell. 4) The SRA (specific radioactivity) of the $^{14}$C-citric acid (Moravek Biochemicals, Inc.; MC-365) working stock is 11,083 cpm/nmol. 5) In order to capture the cells and determine the amount of $^{14}$C uptake, a vacuum manifold is set at 12-15 psi for the filtration (1.2 µm pore size; MF-Millipore™ RAWP02500) and washing of cells.

The PMCT inhibition results for tested compounds are summarized in Table 2.

TABLE 2

| Comp. No. | Inhibitor Concentration (µM) | PMCT Inhibition |
|---|---|---|
| 1 | 5 | 50.1% |
|   | 20 | 75.64% |
|   | 40 | 50.24% |
|   | 200 | 32.09% |
|   | 1000 | 62.8% |
| 2 | 2.8 | 34.7% |
|   | 28 | 24.0% |
|   | 140 | 48.5% |
|   | 280 | 50.0% |
| 3 | 2.8 | 6.2% |
|   | 28 | 9.9% |
|   | 140 | 28.6% |
|   | 280 | 58.7% |
| 4 | 2.8 | -23.2% |
|   | 28 | 28.6% |
|   | 280 | -8.7% |
| 5 | 2.8 | -12.8% |
|   | 28 | -4.5% |
|   | 280 | -3.2% |
| 6 | 2.8 | 9.4% |
|   | 28 | -45.9% |
|   | 140 | 46.8% |
|   | 280 | 70.2%, 87.4% |
| 7 | 2.8 | 28.0% |
|   | 28 | -13.3% |
|   | 140 | 42.5% |
|   | 280 | 62.9%, 77.7% |
| 8 | 2.8 | -41.5% |
|   | 28 | -1.5% |
|   | 280 | 58.4% |
| 9 | 2.8 | 35.7% |
|   | 28 | 1.8% |
|   | 280 | 35.7% |

As can be seen in Table 2, above, certain compounds were found to possess excellent PMCT inhibition activity. For instance, the IC$_{50}$ for compound 1 was found to be 9.8 µM.

Figure 1B:
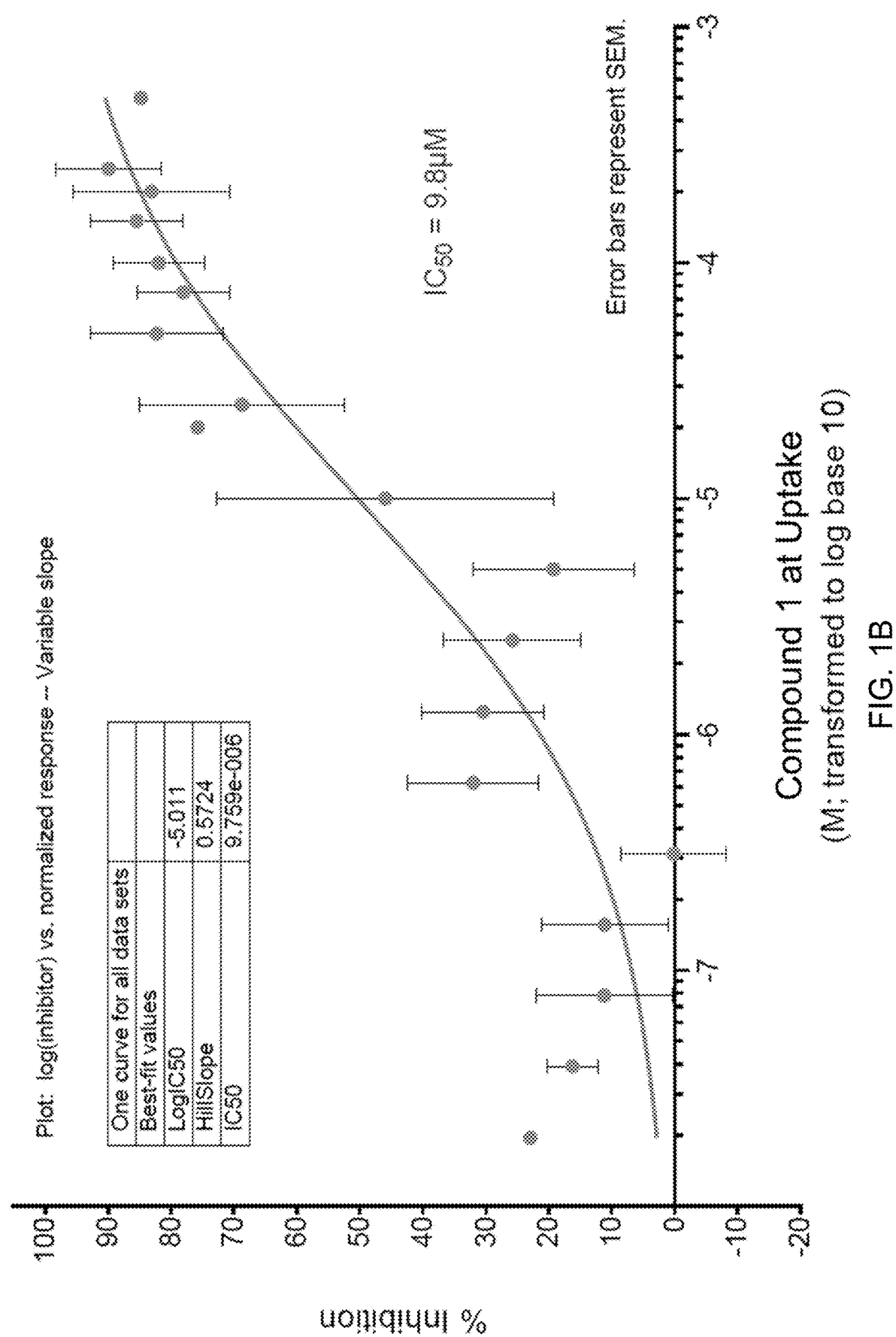

In particular, compounds 1, 2, 3, 6, and 7 exhibited dose-dependent inhibition, even at moderate concentrations (FIG. 1).

Example 3: Anti-Cancer Activity of Compound 1

Based on the results of PMCT inhibition, Compound 1 was selected for anti-proliferative screening against a wide variety of cancerous cell lines across many cancer types, including leukemia, non-small cell lung cancer, colon cancer, CNS cancer, melanoma, ovarian cancer, renal cancer, prostate cancer, and breast cancer.

Figure 2:
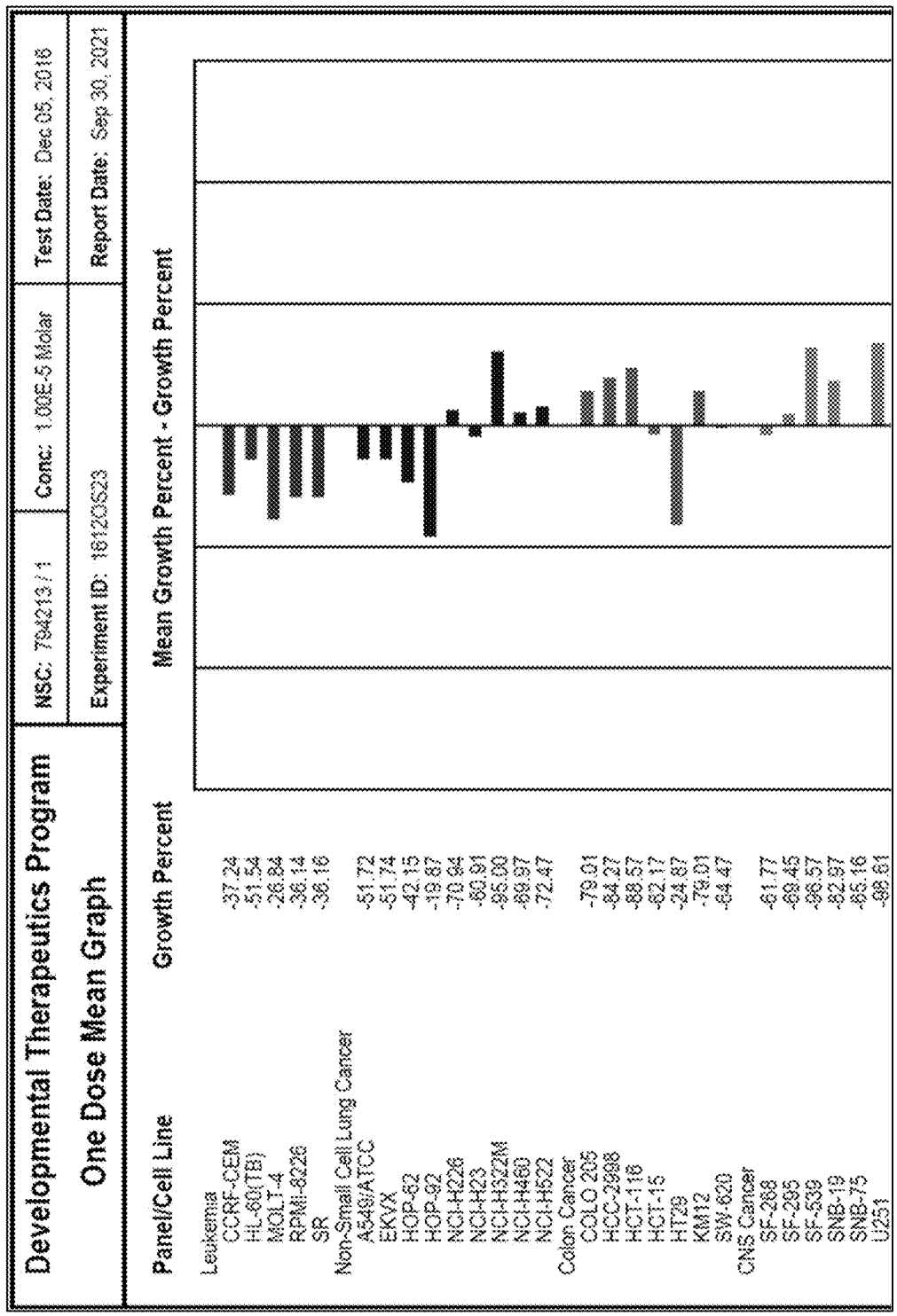
FIG. 2 displays the single-dose growth inhibition of Compound 1 among various NCI cell lines according to an example embodiment.
Figure 2:
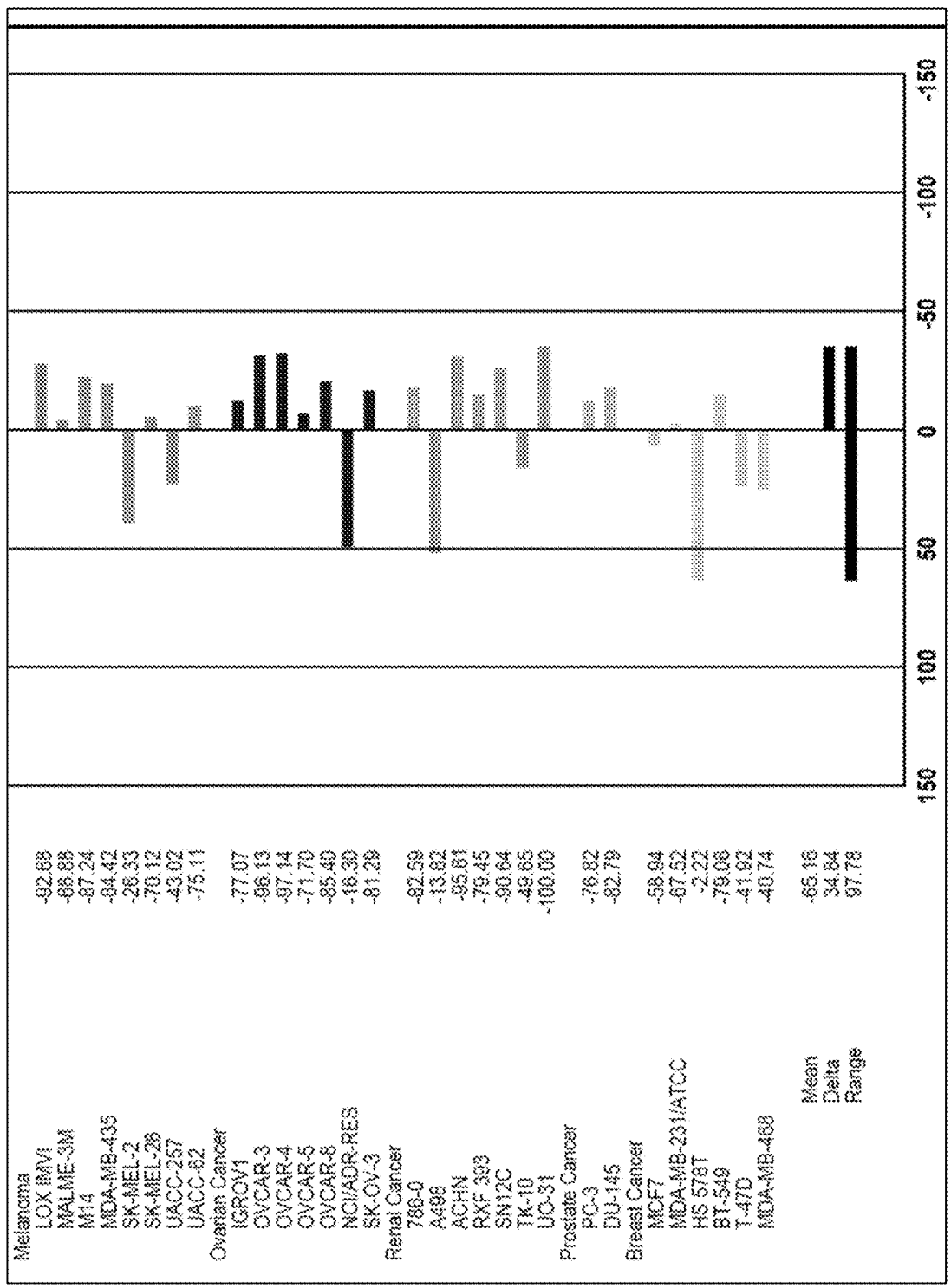
Figure 3:
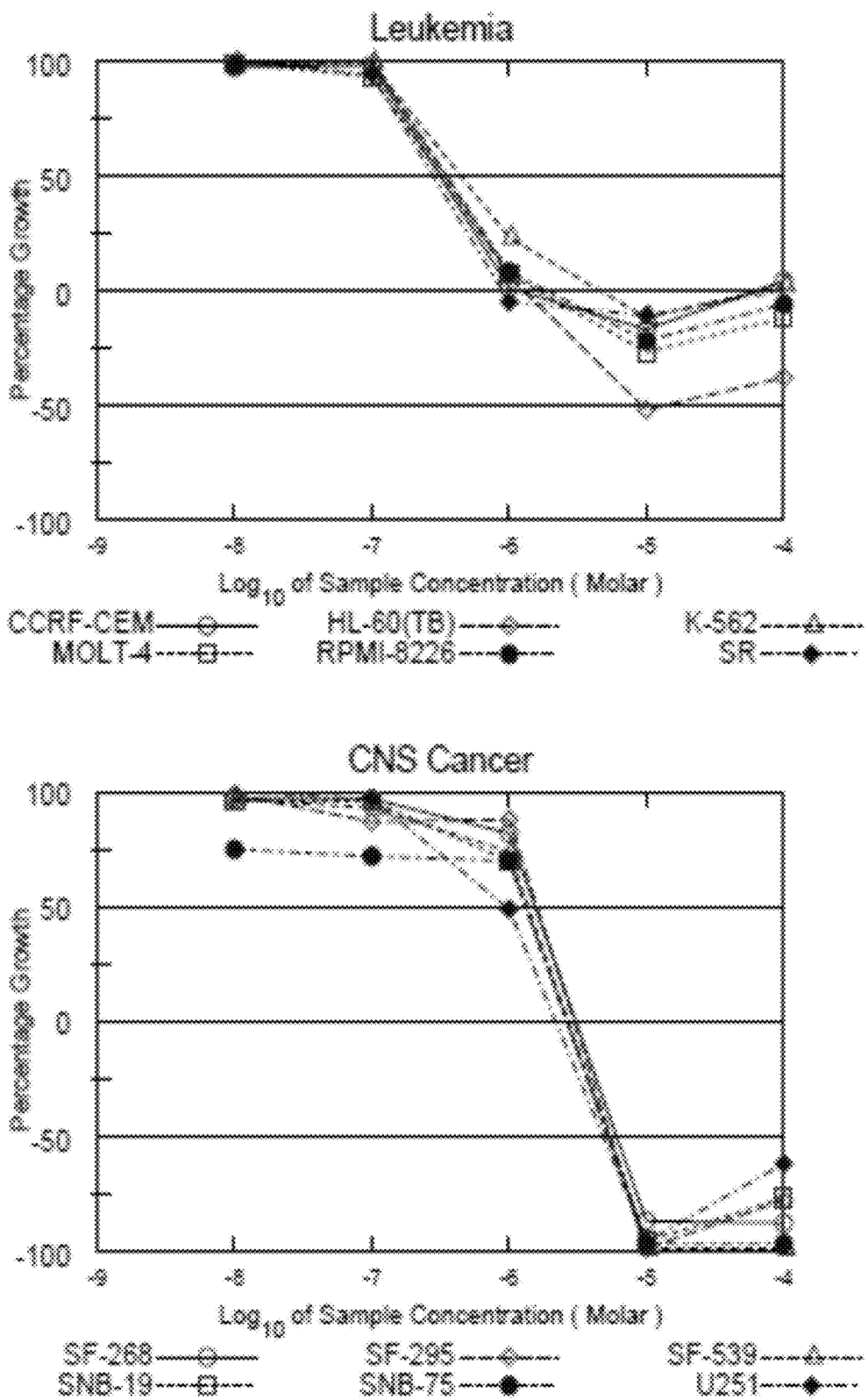
FIG. 3 displays the anti-proliferative activity of Compound 1 among various NCI cell lines according to an example embodiment.
Figure 3:
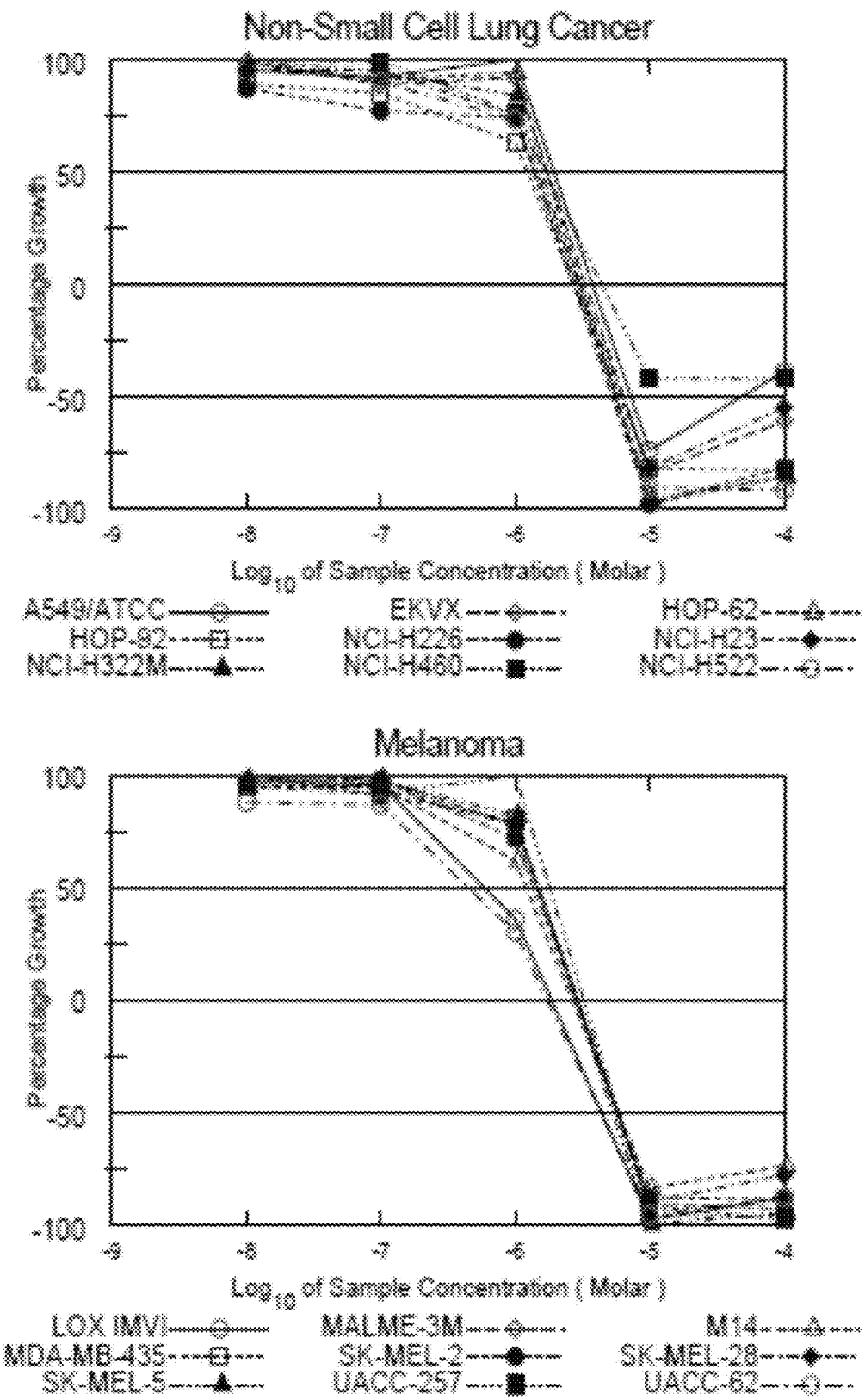
Figure 3:
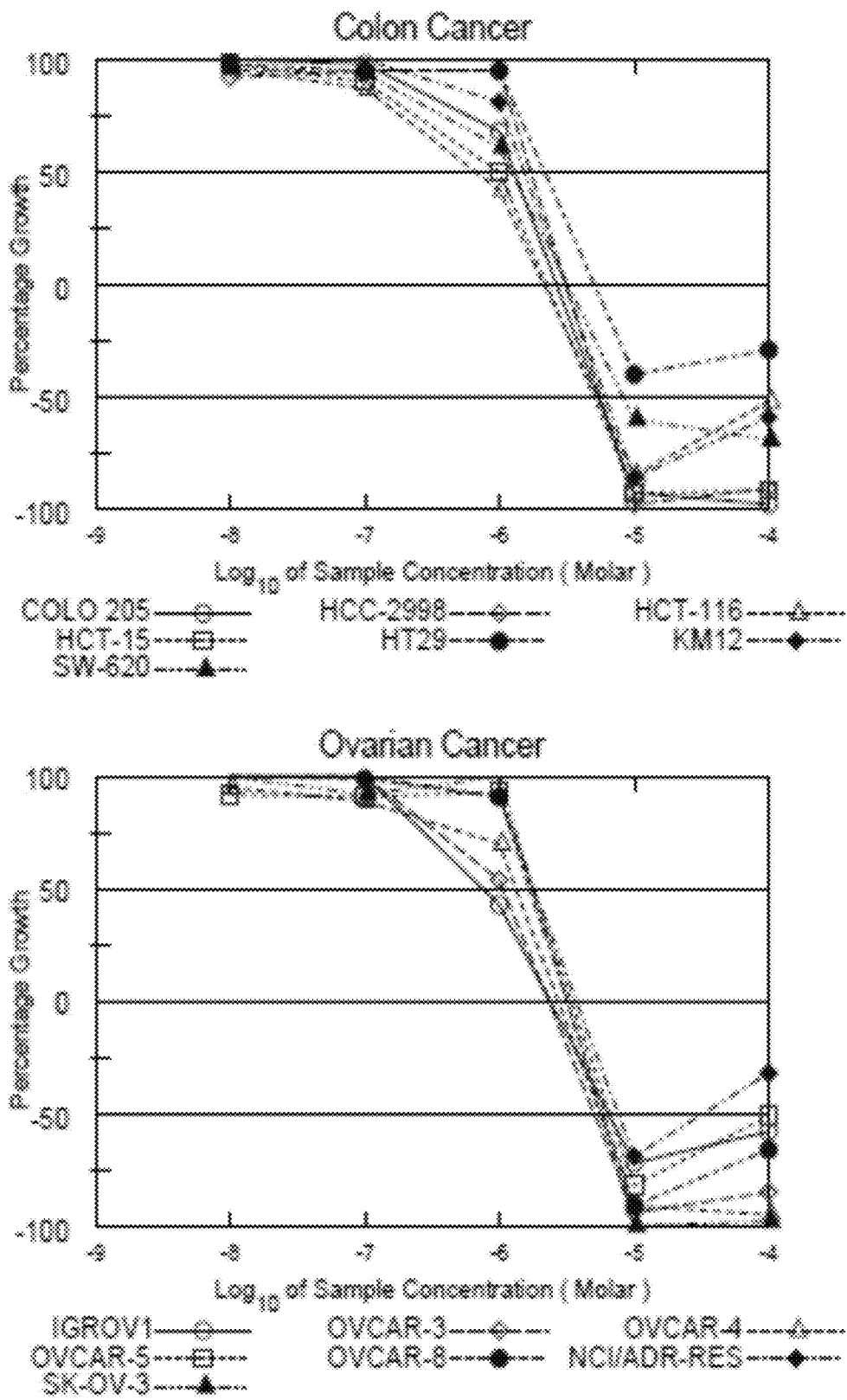
Figure 3:
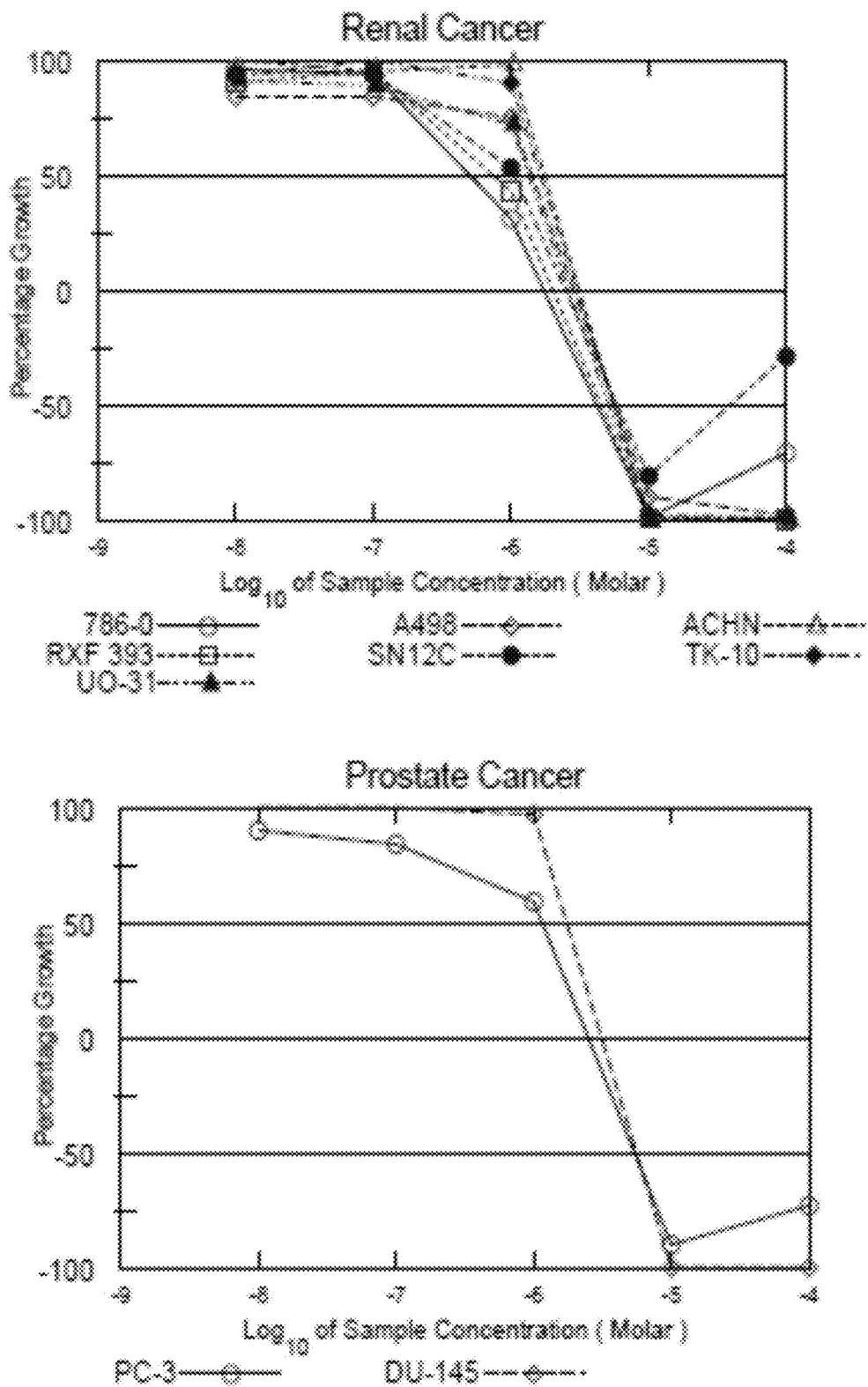
Figure 3:
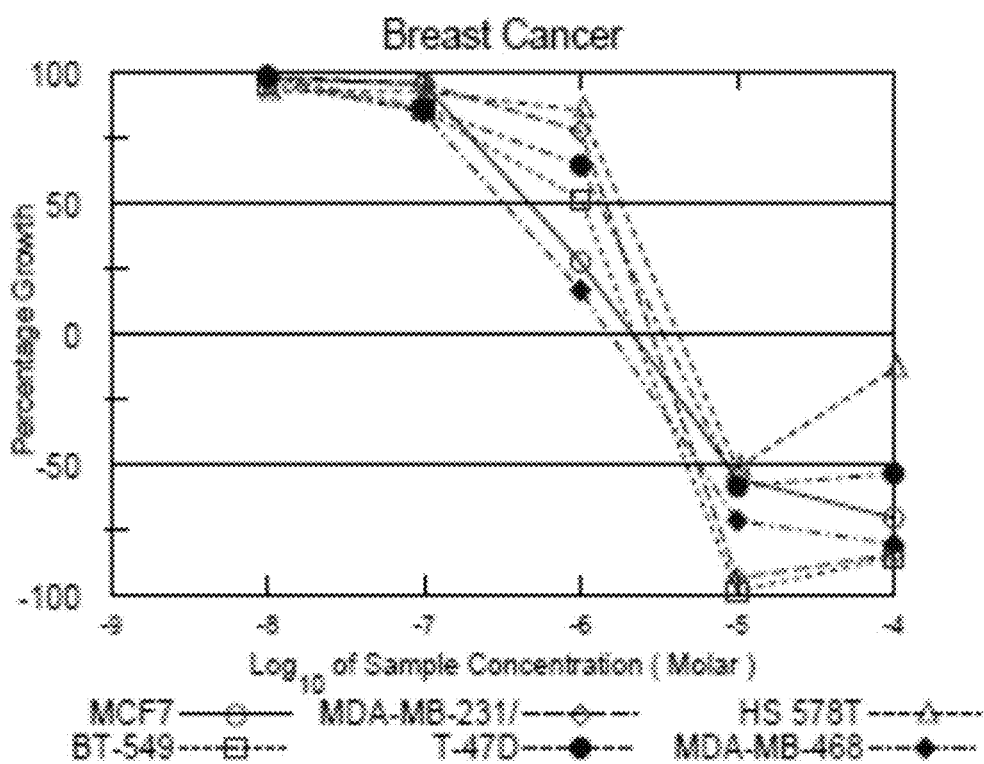

The National Cancer Institute's Developmental Therapeutic preclinical 60 human cancer cell lines were used for an in vitro screen. Results from the NCI 60 cell line assay indicated that Compound 1 demonstrated anti-proliferative activity against nine major cancer cell lines using an initial single dose (FIG. 2) and detailed five dose screening (FIG. 3). The one-dose and five-dose experiments were conducted according to standard NCI protocols.

The one-dose assay reported the growth relative to the no-drug control, and relative to the time zero number of cells. This allowed for the detection of both growth inhibition (values between 0 and 100) and lethality (values less than 0). For example, a value of 100 means no growth inhibition. A value of 40 would mean 60% growth inhibition. A value of 0 means no net growth over the course of the experiment. A value of −40 would mean 40% lethality. A value of −100 means all cells are dead.

As compound 1 exhibited significant growth inhibition in the One-Dose Screen, detailed five-dose screening was also performed. The human tumor cell lines of the cancer screening panel are grown in RPMI 1640 medium containing 5% fetal bovine serum and 2 mM L-glutamine. For a typical screening experiment, cells are inoculated into 96 well microtiter plates in 100 μL at plating densities ranging from 5,000 to 40,000 cells/well depending on the doubling time of individual cell lines. After cell inoculation, the microtiter plates are incubated at 37° C., 5% CO2, 95% air and 100% relative humidity for 24 h prior to addition of experimental drugs.

After 24 h, two plates of each cell line are fixed in situ with TCA, to represent a measurement of the cell population for each cell line at the time of drug addition (Tz). Experimental drugs are solubilized in dimethyl sulfoxide at 400-fold the desired final maximum test concentration and stored frozen prior to use. At the time of drug addition, an aliquot of frozen concentrate is thawed and diluted to twice the desired final maximum test concentration with complete medium containing 50 μg/ml gentamicin. Additional four, 10-fold or ½ log serial dilutions are made to provide a total of five drug concentrations plus control. Aliquots of 100 μl of these different drug dilutions are added to the appropriate microtiter wells already containing 100 μl of medium, resulting in the required final drug concentrations.

Following drug addition, the plates are incubated for an additional 48 h at 37° C., 5% CO2, 95% air, and 100% relative humidity. For adherent cells, the assay is terminated by the addition of cold TCA. Cells are fixed in situ by the gentle addition of 50 μl of cold 50% (w/v) TCA (final concentration, 10% TCA) and incubated for 60 minutes at 4° C. The supernatant is discarded, and the plates are washed five times with tap water and air dried. Sulforhodamine B (SRB) solution (100 μl) at 0.4% (w/v) in 1% acetic acid is added to each well, and plates are incubated for 10 minutes at room temperature. After staining, unbound dye is removed by washing five times with 1% acetic acid and the plates are air dried. Bound stain is subsequently solubilized with 10 mM trizma base, and the absorbance is read on an automated plate reader at a wavelength of 515 nm. For suspension cells, the methodology is the same except that the assay is terminated by fixing settled cells at the bottom of the wells by gently adding 50 μl of 80% TCA (final concentration, 16% TCA). Using the seven absorbance measurements [time zero, (Tz), control growth, (C), and test growth in the presence of drug at the five concentration levels (Ti)], the percentage growth is calculated at each of the drug concentrations levels. Percentage growth inhibition is calculated as:

$[(Ti-Tz)/(C-Tz)] \times 100$ for concentrations for which $Ti >/= Tz$ $[(Ti-Tz)/Tz] \times 100$ for concentrations for which $Ti < Tz$.

Three dose response parameters are calculated for each experimental agent. Growth inhibition of 50% (GI50) is calculated from $[(Ti-Tz)/(C-Tz)] \times 100 = 50$, which is the drug concentration resulting in a 50% reduction in the net protein increase (as measured by SRB staining) in control cells during the drug incubation. The drug concentration resulting in total growth inhibition (TGI) is calculated from Ti=Tz. The LC50 (concentration of drug resulting in a 50% reduction in the measured protein at the end of the drug treatment as compared to that at the beginning) indicating a net loss of cells following treatment is calculated from $[(Ti-Tz)/Tz] \times 100 = -50$. Values are calculated for each of these three parameters if the level of activity is reached; however, if the effect is not reached or is exceeded, the value for that parameter is expressed as greater or less than the maximum or minimum concentration tested.

From the dose response curves three endpoints were calculated: GI50: 50% of growth inhibition; TGI: total growth inhibition; LC50: 50% of lethal concentration. Compound 1 showed low micromolar range growth inhibition towards CCRF-CEM and MOLT-4 ($GI_{50}$: 0.31 μM); HL-60 (TB) ($GI_{50}$: 0.34 μM); K-562 ($GI_{50}$: 0.44 μM); RPMI-8226 ($GI_{50}$: 0.35 μM); SR ($GI_{50}$: 0.27 μM), HCT-116 ($GI_{50}$: 0.68 μM); HCT-15 ($GI_{50}$: 0.97 μM); U251 ($GI_{50}$: 0.95 μM); LOX IMVI ($GI_{50}$: 0.58 μM); UACC-62 ($GI_{50}$: 0.44 μM); IGROV1 ($GI_{50}$: 0.76 μM); 786.0 ($GI_{50}$: 0.49 μM); RFX 393 ($GI_{50}$: 0.45 μM); MCF7 ($GI_{50}$: 0.45 μM) and MDA-MB-468 ($GI_{50}$: 0.32 μM) cell lines (Table 3).

TABLE 3

The NCI 60 cell line screening results of Compound 1 (μM).

| Cell line | $GI_{50}$ | TGI | $LC_{50}$ |
| --- | --- | --- | --- |
| Leukemia | | | |
| CCRF-CEM | 0.31 | — | >100 |
| HL-60 (TB) | 0.34 | 1.27 | — |
| K-562 | 0.44 | — | >100 |
| MOLT-4 | 0.31 | 1.60 | >100 |
| RPMI-8226 | 0.35 | 1.81 | >100 |
| SR | 0.27 | — | >100 |
| Non-small cell Lung | | | |
| A549/ATCC | 2.01 | 3.84 | — |
| EKVX | 1.74 | 3.34 | 6.42 |
| HOP-62 | 1.70 | 3.09 | 5.61 |
| HOP-92 | 1.24 | 2.72 | 5.99 |
| NCI-H226 | 1.37 | 2.68 | 5.23 |
| NCI-H23 | 1.45 | 3.01 | 6.25 |
| NCI-H322M | 1.55 | 2.94 | 5.57 |
| NCI-H460 | 1.66 | 4.38 | >100 |
| NCI-H522 | 1.37 | 2.77 | 5.60 |

TABLE 3-continued

The NCI 60 cell line screening results of Compound 1 (μM).

| Cell line | GI$_{50}$ | TGI | LC$_{50}$ |
|---|---|---|---|
| Colon Cancer | | | |
| COLO 205 | 1.29 | 2.65 | 5.43 |
| HCC-2998 | 1.72 | 3.12 | 5.67 |
| HCT-116 | 0.68 | 2.16 | 5.34 |
| HCT-15 | 0.97 | 2.23 | 5.02 |
| HT29 | 2.16 | 5.04 | >100 |
| KM12 | 1.53 | 3.05 | 6.06 |
| SW-620 | 1.24 | 3.20 | 8.29 |
| CNS Cancer | | | |
| SF-268 | 1.55 | 3.07 | 6.05 |
| SF-295 | 1.60 | 2.96 | 5.48 |
| SF-539 | 1.38 | 2.68 | 5.20 |
| SNB-19 | 1.32 | 2.64 | 5.30 |
| SNB-75 | 1.31 | 2.62 | 5.24 |
| U251 | 0.95 | 2.18 | 4.83 |
| Melanoma | | | |
| LOX IMVI | 0.58 | 1.86 | 4.37 |
| MDA-MB-435 | 1.50 | 2.92 | 5.70 |
| SK-MEL-2 | 1.37 | 2.80 | 5.76 |
| SK-MEL-28 | 1.47 | 2.91 | 5.78 |
| SK-MEL-5 | 1.50 | 2.82 | 5.33 |
| UACC-257 | 1.87 | 3.32 | 5.90 |
| UACC-62 | 0.44 | 1.73 | 4.30 |
| Ovarian Cancer | | | |
| IGROV1 | 0.76 | 2.37 | 6.42 |
| OVCAR-3 | 1.06 | 2.31 | 5.03 |
| OVCAR-4 | 1.33 | 2.73 | 5.59 |
| OVCAR-5 | 1.75 | 3.39 | 6.66 |
| OVCAR-8 | 1.69 | 3.18 | 5.98 |
| NCI/ADR-RES | 1.79 | 3.69 | — |
| SK-OV-3 | 1.81 | 3.20 | 5.66 |
| Renal Cancer | | | |
| 786.0 | 0.49 | 1.73 | 4.20 |
| A498 | 1.42 | 2.85 | 5.73 |
| ACHN | 1.74 | 3.12 | 5.58 |
| RXF 393 | 0.74 | 2.01 | 4.52 |
| SN12C | 1.06 | 2.49 | — |
| TK-10 | 1.63 | 3.01 | 5.55 |
| UO-31 | 1.34 | 2.61 | 5.11 |
| Prostate Cancer | | | |
| PC-3 | 1.16 | 2.49 | 5.37 |
| DU-145 | 1.73 | 3.11 | 5.59 |
| Breast Cancer | | | |
| MCF7 | 0.45 | 2.10 | 8.47 |
| MDA-MB-231/ATCC | 1.43 | 2.81 | 5.51 |
| HS578T | 1.80 | 4.16 | — |
| BT-549 | 1.02 | 2.19 | 4.72 |
| T-47D | 1.30 | 3.31 | 8.43 |
| MDA-MB-468 | 0.32 | 1.53 | 5.62 |

As shown in Table 3, Compound 1 exhibited surprising effectiveness against several cell lines. Critically, GI$_{50}$ values of less than 1 μM were observed in at least one studied cell line of each of leukemia, colon cancer, CNS cancer, melanoma, ovarian cancer, renal cancer, and breast cancer. Indeed, GI$_{50}$ values of less than 0.5 μM were observed for every leukemia cell line studied, demonstrating Compound 1's promise as a potent anti-cancer therapy.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

References

DeBerardinis R J, Chandel N S. Fundamentals of cancer metabolism. Sci Adv. 2016 May 27; 2(5):e1600200.

Hua H, Kong Q, Zhang H, Wang J, Luo T, Jiang Y. Targeting mTOR for cancer therapy. J Hematol Oncol. 2019 Jul. 5; 12(1):71.

Kopel J, Higuchi K, Ristic B, Sato T, Ramachandran S, Ganapathy V. The Hepatic Plasma Membrane Citrate Transporter NaCT (SLC13A5) as a Molecular Target for Metformin. Sci Rep. 2020 May 22; 10(1):8536.

Koundouros N, Poulogiannis G. Reprogramming of fatty acid metabolism in cancer. Br J Cancer. 2020 January; 122(1):4-22.

Li Z, Li D, Choi E Y, Lapidus R, Zhang L, Huang S M, Shapiro P, Wang H. Silencing of solute carrier family 13 member 5 disrupts energy homeostasis and inhibits proliferation of human hepatocarcinoma cells. J Biol Chem. 2017 Aug. 18; 292(33):13890-13901.

Paredes F, Williams H C, San Martin A. Metabolic adaptation in hypoxia and cancer. Cancer Lett. 2021 Apr. 1; 502:133-142.

Pavlova N N, Thompson C B. The Emerging Hallmarks of Cancer Metabolism. Cell Metab. 2016 Jan. 12; 23(1):27-47.

Poolsri W A, Phokrai P, Suwankulanan S, Phakdeeto N, Phunsomboon P, Pekthong D, Richert L, Pongcharoen S, Srisawang P. Combination of Mitochondrial and Plasma Membrane Citrate Transporter Inhibitors Inhibits De Novo Lipogenesis Pathway and Triggers Apoptosis in Hepatocellular Carcinoma Cells. Biomed Res Int. 2018 Jan. 9; 2018:3683026.

Sun J, Aluvila S, Kotaria R, Mayor J A, Walters D E, Kaplan R S. Mitochondrial and Plasma Membrane Citrate Transporters: Discovery of Selective Inhibitors and Application to Structure/Function Analysis. Mol Cell Pharmacol. 2010; 2(3):101-110.

Yang J, Nie J, Ma X, Wei Y, Peng Y, Wei X. Targeting PI3K in cancer: mechanisms and advances in clinical trials. Mol Cancer. 2019 Feb. 19; 18(1):26.

We claim:

1. A compound of formula (I):

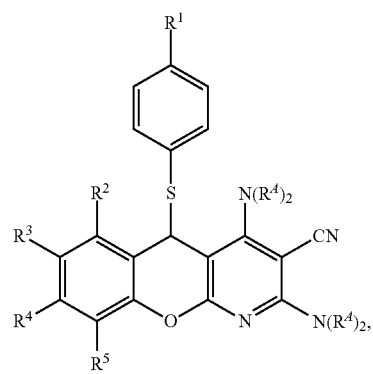

or a pharmaceutically acceptable salt thereof, wherein:
R$^1$ is —OH, —O—(C$_1$-C$_4$ alkyl), or —S—(C$_1$-C$_4$ alkyl);
at least two of R$^2$, R$^3$, and R$^5$ are H, and one of R$^2$, R$^3$, and R$^5$ is —OH, —OCH$_3$ or —O—CH$_2$CH$_3$;
R$^4$ is —OH, (C$_1$-C$_2$ alkyl), —O—(C$_1$-C$_6$ alkyl), or —N—(CH$_2$CH$_3$)$_2$; and
each R$^4$ is independently H or CH$_3$.

2. The compound of claim 1, wherein $R^1$ is —OH, —O—($C_1$-$C_2$ alkyl), or —S—($C_1$-$C_2$ alkyl).

3. The compound of claim 1, wherein $R^1$ is —OH or —O—$CH_3$.

4. The compound of claim 1, wherein $R^1$ is —O—$CH_3$.

5. The compound of claim 1, wherein $R^1$ is —S—$CH_3$.

6. The compound of claim 1, wherein $R^2$ or $R^3$ is —$OCH_3$.

7. The compound of claim 1, wherein $R^4$ is —OH, —$CH_3$, —O—($C_1$-$C_4$ alkyl), or —N—$(CH_2CH_3)_2$.

8. The compound of claim 7, wherein $R^4$ is —OH, —$CH_3$, —O—$CH_3$, or —N—$(CH_2CH_3)_2$.

9. The compound of claim 7, wherein $R^4$ is —OH, —$CH_3$, or —O—$CH_3$.

10. The compound of claim 1, wherein $R^4$ is not —$N(CH_2CH_3)_2$ when $R^1$ is —$OCH_3$ or —$SCH_3$.

11. The compound of claim 1, wherein $R^4$ is H.

12. The compound of claim 1, wherein the compound is of formula (II):

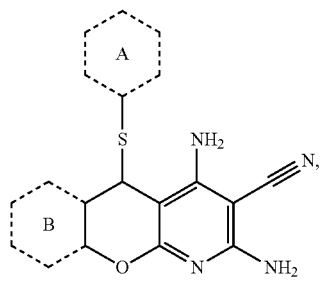
(II)

wherein:
A is

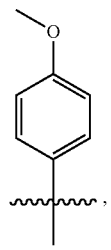, 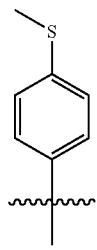, or 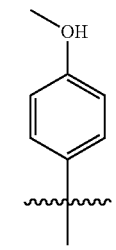;

and
B is

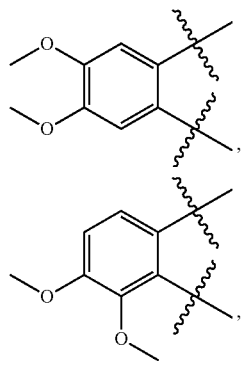,

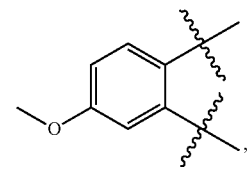,

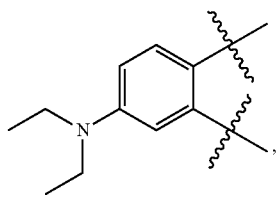,

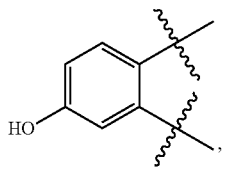, or

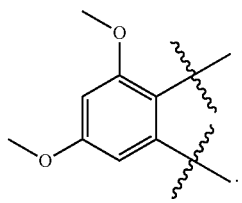.

13. The compound of claim 1, wherein the compound is 2,4-diamino-7,8-dimethoxy-5-((4-methoxyphenyl)thio)-5H-chromeno[2,3-b]pyridine-3-carbonitrile (Compound 1), 2,4-diamino-6,8-dimethoxy-5-((4-methoxyphenyl)thio)-5H-chromeno[2,3-b]pyridine-3-carbonitrile (Compound 2) or 2,4-diamino-7,8-dimethoxy-5-((4-(methylthio)phenyl)thio)-5H-chromeno[2,3-b]pyridine-3-carbonitrile (Compound 6).

14. A compound, or a pharmaceutically acceptable salt thereof, wherein the compound has the structure

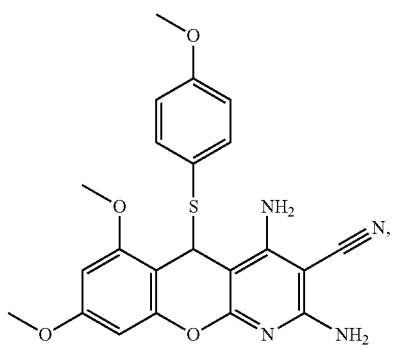
(Compound 1)

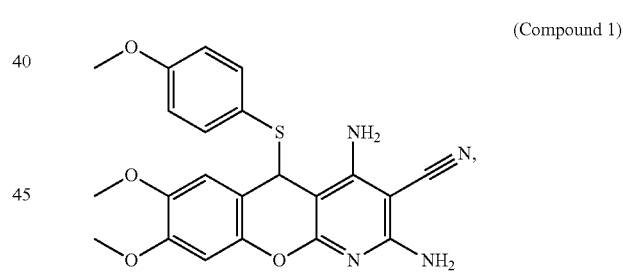
(Compound 2)

-continued

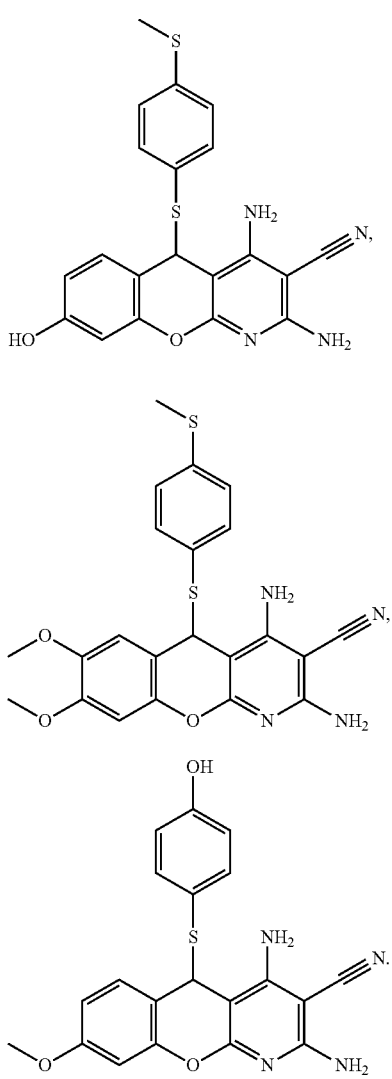

(Compound 3)

(Compound 6)

(Compound 7)

15. The compound of claim 1, wherein the compound has the structure

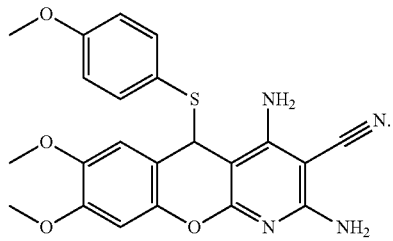

(Compound 1)

16. A method of treating cancer in a subject in need thereof, comprising administering a therapeutically effective amount of the compound of claim 1 to the subject, wherein the cancer is leukemia, non-small cell lung cancer, colon cancer, CNS cancer, melanoma, ovarian cancer, renal cancer, prostate cancer, or hepatocellular carcinoma.

17. The method of claim 16, wherein the compound is administered in a dosage in the range of 0.1 mg/kg to 400 mg/kg.

18. A method of treating cancer in a subject in need thereof, comprising administering a therapeutically effective amount of the compound of claim 14 to the subject, wherein the cancer is leukemia, non-small cell lung cancer, colon cancer, CNS cancer, melanoma, ovarian cancer, renal cancer, prostate cancer, or hepatocellular carcinoma.

19. The method of claim 18, wherein the compound is administered in a dosage in the range of 0.1 mg/kg to 400 mg/kg.

* * * * *

UNITED STATES PATENT AND TRADEMARK OFFICE
CERTIFICATE OF CORRECTION

PATENT NO. : 11,814,392 B2
APPLICATION NO. : 17/514378
DATED : November 14, 2023
INVENTOR(S) : Mayor et al.

Page 1 of 1

It is certified that error appears in the above-identified patent and that said Letters Patent is hereby corrected as shown below:

In the Specification

Column 4, Lines 45-55, the third structure should read:

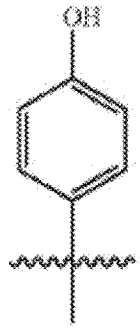

In the Claims

Column 29, Lines 37-47, the third structure should recite:

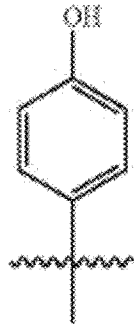

Signed and Sealed this
Twelfth Day of November, 2024

Katherine Kelly Vidal
Director of the United States Patent and Trademark Office